US010317661B2

(12) United States Patent
Ewoniuk et al.

(10) Patent No.: US 10,317,661 B2
(45) Date of Patent: Jun. 11, 2019

(54) AUTOMATED COVERSLIPPER AND METHODS OF USE

(71) Applicant: Ventana Medical Systems, Inc., Tucson, AZ (US)

(72) Inventors: Aaron Michael Ewoniuk, Tucson, AZ (US); Charles Nathan Hassen, Tucson, AZ (US); Michael Mensah, Tucson, AZ (US); Logan Rivas, Tucson, AZ (US); DuWayne Dennis Snyder, Eloy, AZ (US); Kenneth Eugene Stumpe, Tucson, AZ (US); Michael Thompson, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 183 days.

(21) Appl. No.: 15/399,948

(22) Filed: Jan. 6, 2017

(65) Prior Publication Data

US 2017/0115476 A1   Apr. 27, 2017

Related U.S. Application Data

(63) Continuation of application No. PCT/EP2015/065407, filed on Jul. 7, 2015.

(Continued)

(51) Int. Cl.
*G02B 21/34* (2006.01)
*G01N 35/00* (2006.01)

(52) U.S. Cl.
CPC ....... *G02B 21/34* (2013.01); *G01N 35/00029* (2013.01); *G01N 2035/00138* (2013.01);

(Continued)

(58) Field of Classification Search
CPC ......... Y10T 156/1132; Y10T 156/1137; Y10T 156/1939; Y10T 156/1944
See application file for complete search history.

(56) References Cited

U.S. PATENT DOCUMENTS 4,428,793 A * 1/1984 Sato .................... B65H 3/0816
156/285
5,989,386 A   11/1999 Elliott
(Continued)

FOREIGN PATENT DOCUMENTS

JP   53-104586   8/1978
JP   57-191736   12/1982
(Continued)

OTHER PUBLICATIONS

Machine translation from Google Patents, JP2005-317273A (Year: 2005).*

(Continued)

*Primary Examiner* — Mark A Osele
(74) *Attorney, Agent, or Firm* — Ventana Medical Systems, Inc.

(57) ABSTRACT

An apparatus and method for selecting and dispensing coverglasses over specimens on slides for the purpose of viewing specimens through a microscope. The selecting device contains suctioning mechanisms for picking up a coverglass from a stack of coverglasses. It also contains the ability to shape the coverglass to assist in separating and laying down of the coverglasses with a reduction in the creation of bubbles in the fluid.

21 Claims, 18 Drawing Sheets

Related U.S. Application Data

(60) Provisional application No. 62/044,105, filed on Aug. 29, 2014, provisional application No. 62/022,474, filed on Jul. 9, 2014.

(52) U.S. Cl.
CPC ............... *G01N 2035/00168* (2013.01); *Y10T 156/1132* (2015.01); *Y10T 156/1944* (2015.01)

(56) References Cited

U.S. PATENT DOCUMENTS

| | | | |
|---|---|---|---|
| 6,345,818 B1 * | 2/2002 | Stephan | B25J 15/0052 |
| | | | 271/106 |
| 6,382,693 B1 * | 5/2002 | Ljungmann | B25J 15/0616 |
| | | | 294/188 |
| 6,431,623 B1 * | 8/2002 | Roeters | B65G 47/91 |
| | | | 271/90 |
| 6,759,011 B1 | 7/2004 | Richards et al. | |
| 6,796,353 B2 | 9/2004 | Lang et al. | |
| 7,271,006 B2 | 9/2007 | Reinhardt et al. | |
| 7,468,161 B2 | 12/2008 | Reinhardt et al. | |
| 7,727,774 B2 | 6/2010 | Reinhardt et al. | |
| 8,048,373 B2 | 11/2011 | Reinhardt et al. | |
| 10,156,503 B2 * | 12/2018 | Thompson | G01N 1/312 |
| 2003/0047863 A1 | 3/2003 | Lang et al. | |
| 2004/0016506 A1 | 1/2004 | Sakayori et al. | |
| 2005/0135918 A1 * | 6/2005 | Tominaga | B65H 3/0816 |
| | | | 414/795.7 |
| 2005/0236101 A1 | 10/2005 | Kobayashi | |
| 2011/0305842 A1 * | 12/2011 | Kram | G01N 1/2813 |
| | | | 427/355 |

FOREIGN PATENT DOCUMENTS

| | | | |
|---|---|---|---|
| JP | 11-514102 A | | 11/1999 |
| JP | 2002-216958 A | | 8/2002 |
| JP | 2003-156692 A | | 5/2003 |
| JP | 2005-523857 | | 8/2005 |
| JP | 2005-317273 A | | 10/2005 |
| JP | 2005300972 A | * | 10/2005 |
| JP | 3986383 B2 | * | 10/2007 |
| JP | 2011-089932 A | | 5/2011 |
| WO | 9520176 A1 | | 7/1995 |

OTHER PUBLICATIONS

International Search Report and Written Opinion dated Dec. 9, 2015 in corresponding PCT/EP2015065407, pp. 1-9.

* cited by examiner

AUTOMATED COVERSLIPPER AND METHODS OF USE

CROSS-REFERENCE TO RELATED APPLICATIONS

This patent application is a continuation of International Patent Application No. PCT/EP2015/065407, filed Jul. 7, 2015, which claims priority to and the benefit of U.S. Provisional Application No. 62/022,474, filed Jul. 9, 2014 and U.S. Provisional Application No. 62/044,105, filed Aug. 29, 2014. Each of the above patent applications is incorporated herein by reference as if set forth in its entirety.

TECHNICAL FIELD

This disclosure relates to methods and apparatuses for automatically covering a specimen to be examined on a microscope with a coverslip.

BACKGROUND

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

Biological samples/specimens, e.g., tissue sections or cells, are often mounted on microscope slides for examination. While on the slide, the specimens are often treated with one or more substances (e.g., dyes, reagents, etc.) to add color and contrast or microscopically labeled reagent to otherwise transparent or invisible cells or cell components. The treated specimens are often then covered with a thin transparent coverslip. This is done for several reasons. The coverslip can flatten the specimen so that the specimen is in the same viewing plane, thereby allowing one to view the specimen better. The coverslip provides protection for the specimen from the objective lens of the microscope should the lens be placed too closely to the slide. The coverslip (often in combination with an adhesive) further provides a housing structure or an area by which the specimen will be permanently retained on the slide to preserve for study and archiving purposes. The coverslip also helps to avoid contamination of the specimen.

The coverslip is typically a thin, rectangular, square or round piece of glass or plastic which is placed in direct contact with and over the specimen on the slide. The coverslip comes in a variety of sizes and shapes. One example of the coverslip has dimensions of about 1 in.×2 in. (25.4 mm×50.8 mm) and 0.005 in to 0.009 in (0.127 mm to 0.2286 mm) thick. They are often packaged stacked flat in a vertical pile. However, the coverslips are difficult to handle and separately remove from the stack as they are fragile and can stick together easily or break. To remove a coverslip from a stack, a considerable amount of bending moment is often applied to the coverslip. For example, previous systems, such as shown in U.S. Pat. No. 5,989,386 (Elliott), use two suction cup devices on a coverslip, placed on both sides of the middle of the coverslip. The suction cups thereafter bend the coverslip around a center element, creating great stress in the middle of the coverslip to separate it from the stack of coverslips. This action can result in numerous coverslips breaking because they are very fragile and the force applied was greater than the stability of the coverslip. The bending force causes a disproportionate amount of stress at the center of the coverslip. The bending action also does not guarantee that only one coverslip is selected.

Automated coverslippers have been used to mount glass coverslips on specimen-bearing microscope slides. However, such automated coverslippers can pick up more than one coverslip as they frequently stick together due to static forces, van der Waals forces, or moisture between adjacent coverslips. This may result in two or more coverslips being mounted on a slide. It may also be difficult to remove the excess coverslip(s) from the slide. If the automated coverslipper attempts to transport stuck-together slides, coverslips may drop resulting in loose coverslips in automated processing equipment. The loose coverslips can result in damage or malfunction of the automated processing equipment and may result in "downtime" for maintenance. Automated coverslippers are also not capable of accurately counting coverslips during handling. In addition, placement of the coverslip on the slide (often in the presence of a fluid, e.g., liquid adhesive) presents further problems. For example, it is important that no splashing occurs or no air bubbles be entrained between the coverslip and slide and become trapped under the coverslip when placed onto the slide. Examples of automated systems, such as shown in U.S. Pat. No. 7,271,006 (Reinhardt) and U.S. Pat. No. 7,727,774 (Reinhardt), use suctioning mechanisms for picking up and laying down a coverslip and a bending mechanism to assist in separating the coverslips. However, such devices can result in the unfortunate occurrence of bubbles that obfuscate subsequent analysis of the specimen on the slide.

Also, it is important not to harm the specimen in any way when positioning the coverslip onto the slide. One way to apply the coverslip is to place the coverslip on the slide, and then apply pressure onto the coverslip to compress and remove trapped air bubbles. However, handling and separating the coverslips at times can also charge them with static electricity. Electrostatic forces can hold the coverslip to the suction cups even after turning the mechanism off, making it difficult to apply the coverslip to the slide or discharge as the coverslip approached the slide causing one or more bubbles to form. Further, compression of the coverslip to remove air bubbles may cause the adhesive on the tissue sample to expel outward, thereby potentially contaminating other slides or other portions of the machine. Thus, there exists a need to provide a better automated coverslipper.

Thus, the art fails to provide an automated coverslipper and automated method of coverslipping with reduced bubbles and control of on-slide fluids. Nor does the current art provide an ability to configure or induce varied shapes in a coverslip that enable these advantages.

SUMMARY OF TECHNOLOGY

The present disclosure relates to an automated system, device, and process for placing coverslips on specimen-bearing microscopic slides. At least one embodiment comprises a coverslipper configured to pick up a single coverslip and then place the coverslip on specimen-bearing slides, while reducing, and/or eliminating, the splashing, contamination, or the entraining of bubbles during coverslip application. The system enables high sample throughput while minimizing or limiting the potential for cross-contamination of slides.

At least one embodiment relates to an automated coverslipper for mounting a coverslip on a slide, comprising: (i) at least one coverslip; (ii) at least one slide containing a biological specimen; and (iii) at least one lifter head comprising a plate having a bottom surface with at least three individually controlled suction cups arranged thereon, each the suction cup being fluidly connected, by way of a gas conduit, to a pneumatics module, which includes a vacuum source, a pressure source, a pressure sensor, and an independently operable control-valve for each gas conduit, said pneumatics module being configured to supply an independent vacuum or pressurized gas to each suction cup to enable the lifter head to pick up, transport, and deposit the coverslip on the slide, and wherein the at least one of said independent control-valve is configured to allow an immediate release of vacuum and a gradual release of vacuum.

In one embodiment, the coverslipper further comprises: (i) a transporter coupled to a motor and attached to, and suspending, the lifter head in a substantially vertical position, and configured to move the lifter head horizontally, vertically, or diagonally to position the bottom surface of the lifter head over a coverslip; and (ii) a control module in electrical communication with the transporter, the lifter head, the pneumatics module, and the suction cups, wherein the control module coordinates all functions of or interactions with each of the components of the coverslipper.

In one embodiment the coverslipper is configured to move the lifter head to a position over a slide. In another embodiment the coverslipper is configured to receive a slide that is moved under the lifter head.

In one embodiment, the coverslipper further comprises: (i) at least one fluid dispenser associated with the lifter head and in fluid communication with a fluidics module that supplies a reagent to the fluid dispenser, said fluid dispenser configured to dispense fluid on the slide; and (ii) at least one gas knife associated with the lifter head and in fluid communication with a pneumatics module and configured to provide gas to the top surface of a slide; (ii) wherein the fluid dispenser and the gas knife are suspended in a substantially vertical position and the fluid dispenser and gas knife are configured to move with the lifter head, and wherein the fluid dispenser and said gas knife are in electrical communication with the control module. In one embodiment, the at least one fluid dispenser and the at least one gas knife are associated with each other and the lifter head. In a further embodiment the association of the at least one fluid dispenser and the at least one gas knife can be a physical coupling.

In one embodiment, the coverslipper further comprises at least one slide tray holding, in a substantially horizontal position, at least two slides arranged in at least one row; and at least one cartridge containing a plurality of coverslips vertically stacked and arranged so the top most coverslip of the stack is accessible to the lifter head via a top opening in the cartridge.

In another embodiment the coverslipper has two the lifter heads configured and positioned in tandem to work simultaneously or independently on at least two rows of slides.

In one embodiment, the bottom surface of the lifter head has a shape selected from the group consisting of flat, concave, convex, dual chamfer and combinations thereof.

In one embodiment, the lifter head is configured to provide, either simultaneously or sequentially, an independent vacuum to each of the three suction cups to thereby hold the coverslip in various configurations to the bottom surface of the lifter head.

In other embodiments each lifter head is configured with one or more vacuum sensors to measure pressure in the activated suction cups to determine if the suction-lifted coverslip is broken. For example, a vacuum sensor is attached to a common manifold that provides a single pressure reading for all three suction cups (cups) on the lifter head. In this manner, each lifter head with its own vacuum pump is measured individually. In one embodiment, three sensing times are used starting with separation detection of contact between the coverslip and suction cup during descent into the cassette. That is the first use of the pressure threshold sensor. Second time occurs when the coverslip is peeled away from stack, during holding by all three suction cups; this is where the second check of pressure happens. This determines if the coverslip is broken. The third time occurs during the laydown, during cantilever on the other side of the head (in reverse peel action). This is when the third pressure check happens. This process of measuring pressure can also detect a broken coverslip on top of a full one. In one embodiment, this is why pressure is let go (bleed off pressure) with one end; this is when the broken piece will fall. This maximizes the chances of shaking off a broken piece before the suction up. In this manner, the vacuum sensor measures pressure to determine if the average pressure is under threshold.

In one embodiment, when the lifter head transports the suction-lifted coverslip and positions it over a slide, a control module then initiates a laydown protocol to lay down the lifted coverslip. A cantilevered configuration is achieved by applying suction to only one of the three suction cups, resulting in a geometry in which the coverslip hangs at an angle relative to the horizontal plane of the specimen slide. In this manner, the three suction cups on the lifter head are configured to perform a cantilever laydown of a single coverslip that is being held to the bottom surface of the lifter head by vacuum suction of an end suction cups so one end of the coverslip is first laid onto the slide and the remainder of the coverslip is then rolled down onto the slide and thereby inducing a curvature in the coverslip. In one embodiment, a gradual bleed of vacuum happens at the final release. Such a bleed of suction can be achieved by use of an orifice in smaller than that used to apply the suction or the control valve could be configured to achieve such a reduced vacuum release rate.

In one other embodiment, a lifter head can have a center concave lifter shape to the lifter head, a dual chamfer narrow lifter head design or shape, a dual chamber wide lifter head shape/design, or a flat square-like or flat rectangular lifter head shape/design without chamfer.

In one embodiment, the method for performing a laydown of a single coverslip, comprises: positioning a suction lifted coverslip over the slide, wherein the suction lifted coverslip is held to a bottom surface of a lifter head by a vacuum in three individually controlled suction cups arranged on said bottom surface, wherein each suction cup is fluidly connected, by way of a gas conduit, to a pneumatics module, which includes a vacuum source, one or more vacuum sensors, and a control-valve for each gas conduit, wherein said pneumatics module is supplying an independent vacuum to each of said three suction cups thereby holding said coverslip to the bottom surface; removing the vacuum in two of the suction cups so the coverslip is held at one end only by the one suction cup that still has a vacuum; lowering the coverslip to the surface of the slide until a bend is induced in the coverslip thereby creating fluid movement across the surface of the slide whereby the coverslip is continually lowered and a wavefront of fluid created on the slide as the fluid is gently pushed from one end of slide to the other end and thereby inducing a curvature in the coverslip; and releasing the held end of the slide by activating the vacuum valve to the suction cup holding the coverslip such that the vacuum is removed at a gradual release rate as opposed to an abrupt release.

DETAILED DESCRIPTION OF TECHNOLOGY

Figure 1:
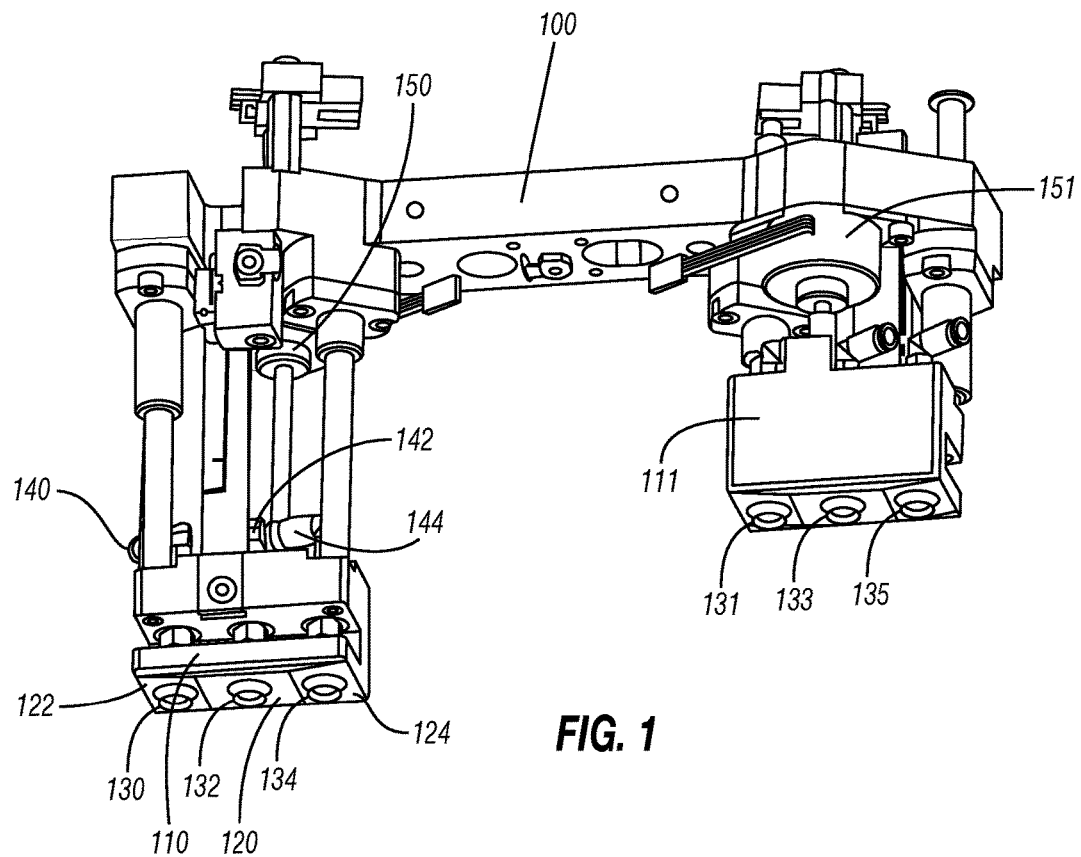
FIG. 1 depicts a perspective view of one embodiment of the invention in which an assembly plate 100 of an automated coverslipper contains two lifter heads 110, 111.

Detailed descriptions of one or more embodiments are provided herein with reference to the accompanying drawings, in which the embodiments are shown. It is to be understood, however, the compositions, elements, devices, systems, and methods of the disclosure may be embodied in many different forms and should not be construed as being limited to the embodiments set forth herein. The specific details disclosed herein are not to be interpreted as limiting, but rather as a representative basis for the claims and for teaching one skilled in the art to employ the disclosed compositions, devices, systems and methods in any appropriate manner. The embodiments are provided so this disclosure will be thorough and complete, and will fully convey the concept of the disclosure to one skilled in the art. Furthermore, all titles of sections contained herein are not to be construed as limitations on the invention, rather they are provided to structure the illustrative description of the invention that is provided by the specification. Also, in order to facilitate understanding of the various embodiments, the following explanations of terms is provided.

When the phrase "for example," "such as," "such that," "including", and the like are used, the phrase "and without limitation" is understood to follow unless explicitly stated otherwise. Similarly, "an example," "exemplary", and the like are understood to be non-limiting.

The term "substantially" allows for deviations from the descriptor that do not negatively impact the intended purpose. Descriptive terms are understood to be modified by the term "substantially" even if the word "substantially" is not explicitly recited.

The term "about" is meant to account for variations due to experimental error. All measurements or numbers are implicitly understood to be modified by the word about, even if the term "about" is not explicitly recited for such.

The terms "comprising" and "including" and "having" and "involving" and the like are used interchangeably and have the same meaning. Similarly, "comprises", "includes," "has," and "involves" and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c.

The singular forms "a," "an," and "the" include plural referents unless the context clearly indicates otherwise. In this regard, where ever the terms "a" or "an" or "the" are used, "one or more" is understood unless explicitly stated otherwise or such interpretation is nonsensical in context.

The term "associated with" or "associated therewith" means that two or more items work or move or operate together, independently, sequentially, or in tandem. These elements may also be physically or electronically connected to one or more of each other so one follows in proximity to another. An associated element may also be physically coupled together.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Often during the coverslipping process, bubbles can be generated and trapped by fluid turbulence, eddy current, surface roughness of pre-dried adhesive on the bottom of coverslip and by electrostatic charge. The present disclosure relates to an automated system and method for picking up and mounting coverslips on specimen-bearing microscope slides, while minimizing or eliminating splashing, contamination and the entraining of bubbles in fluid on the specimen-bearing surface of slides. At least one embodiment includes an automated coverslipper apparatus to dissuade fluid bubbling under the coverslip during coverslip application. A coverslipper of the present disclosure, see for example FIG. 15, is configured to use a precisely controlled cantilevered coverslipping laydown process to create fluid movement. This disclosed coverslipper achieves this by utilizing three individually plumbed and controlled suction cups (3 suction cups per lifter head), control valves, and bleed-off valves that, along with optional, mechanically pulsed movements, allow for a single coverslip to be laid down slowly on a microscope slide containing a specimen and on-slide fluid in a manner so that the coverslip is laid down behind the wavefront of fluid created on the on-slide end of the coverslip and is gently pressed to the other end in a cantilever laydown process. As a result, the timing and control of the fluid wavefront (such as the moving meniscus 1714 in FIG. 14) enables bubbles that ride the inertia of bulk fluid translating from the distal to label end of the slide to surface escape into the air before the final corner of the coverslip touches down.

In one embodiment the coverslip is retained/held only by one end. At the free hanging end of the coverslip the coverslip is bowed as either the coverslip is lowered or the slide is elevated. This bowing results in increase potential energy within the structure of the coverslip. By controlling the release of the retained end of the coverslip by gradually reducing the "bow" in the coverslip, i.e., reduction of the potential energy within the coverslip, the end can be gradually released concurrently with the reduction of energy so the and does not "slap" the fluid on the slide or the slide surface. This carefully controlled and purposely slow laydown process of lowering and release of a coverslip onto the slide significantly reduces the formation of bubbles in the fluid under the coverslip. This process can take up to about 15 seconds per slide. In one embodiment the slowest speed of travel is 0.005 in./sec. (0.127 mm/sec.) but it is recognized that the laydown process speeds are dependent upon the multiple factors previously mentioned. This laydown process produces a flat meniscus that is optimal for the elimination of bubbles that might otherwise (for example, with a parabolic meniscus) arise. The coverslipper is also capable of applying bursts of deionized air through the individually plumbed and controlled suction cups (3 suction cups on a lifter head) to further discourage bubbles or static events and to squeeze out remaining excess fluid from under the coverslip.

Figure 2:
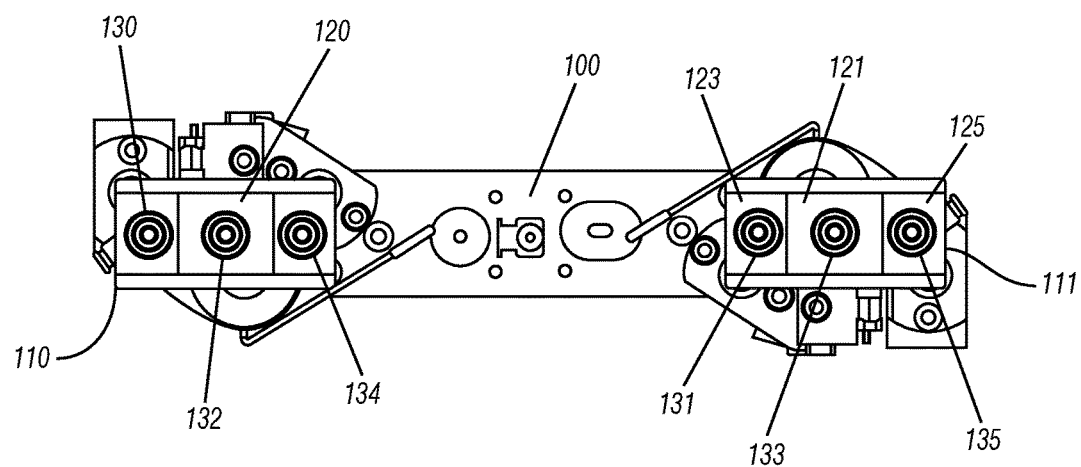
FIG. 2 depicts a bottom view of the invention in which assembly plate 100 of an automated coverslipper contains two lifter heads 110, 111.

FIGS. 1 and 2 show one embodiment of the present invention in which assembly plate 100 supports a first lifter head 110 and a second lifter head 111. The assembly plate may also support more or fewer lifter heads than shown in FIG. 1. Lifter head 110 has three suction cups 130, 132, 134 extending from its bottom surface 120. Bottom surface 120 comprises chamfers 122, 124 about suction cups 130, 134, respectively. Gas conduit 140 fluidly connects suction cup 130 to a pneumatics module (not shown), allowing a vacuum, atmospheric pressure, or increase pressure to be applied at suction cup 130. Similarly, gas conduits 142, 144 fluidly connect suction cups 132, 134 to the pneumatics module (not shown). Lifter head 111 also has three suction cups 131, 133, 135 extending from bottom surface 121. This bottom surface 121 features chamfers 123, 125. Stepper motors 150 and 151, mounted on assembly plate 100 allow the lifter heads 110, 111 to be selectively raised and lowered.

FIG. 2 provides an inverted perspective view of the assembly plate 100 shown in FIG. 1 and lifter heads 110, 111.

Figure 3A:
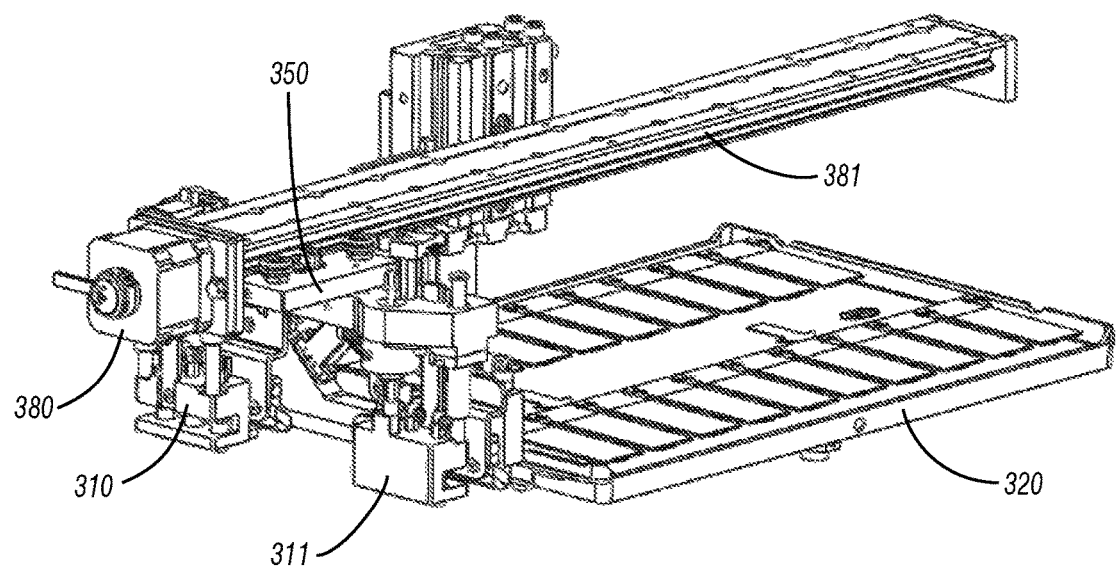
FIGS. 3 A-B depict two perspective views of a further embodiment of an automated coverslipper in which two lifter heads 310, 311 are reciprocatingly mounted to a stepper motor 380 and lead screw 381 assemblies.
Figure 3B:
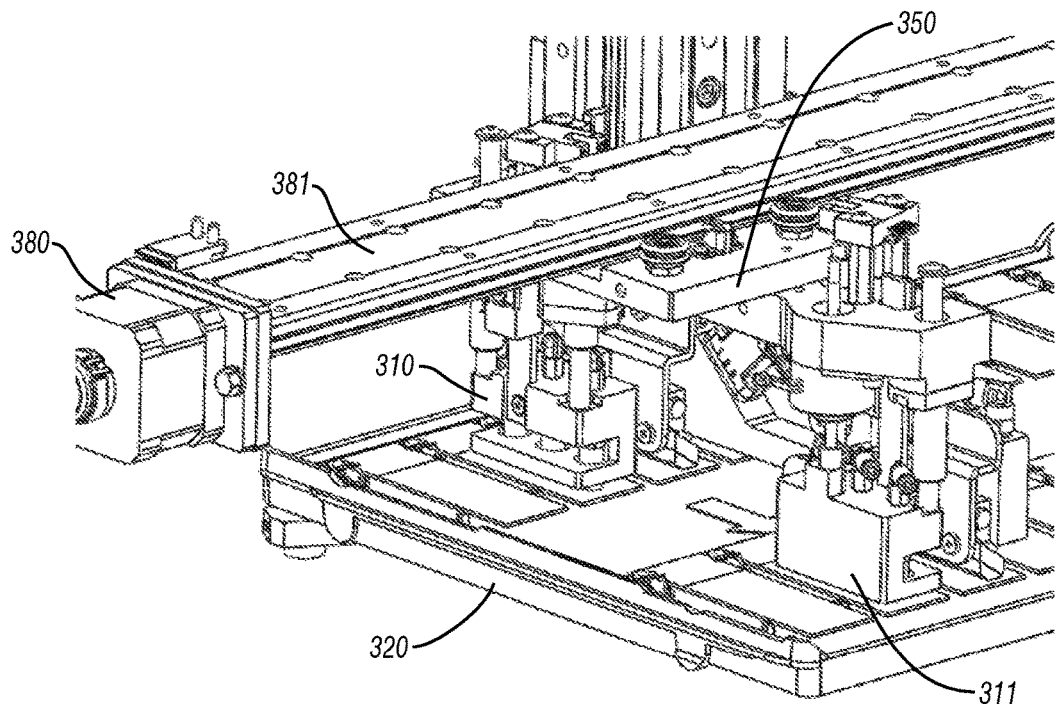

FIG. 3 provides two perspective views of an embodiment having lifter heads 310, 311 reciprocally mounted to a transport carriage 350 using a stepper motor 380 and lead screw assembly 381. When stepper motor 380 is activated, lifter heads 310, 311 move relative to specimen tray 320. Support mechanisms provide a place for a tray 320 to hold slides so the lifter heads 310, 311 can select, transport, and mount coverslips on the slides. Suction cups on lifter head 310, and suction cups on lifter head 311, protrude from the lower surfaces of lifter heads 310 and 311. Top view in FIG. 3A shows the transport carriage 350 with attached support block moved away from the tray 320, while the lower view in FIG. 3B shows the carriage positioned over the tray 320 to allow each of the lifter heads 310 and 311 to apply a coverslip to one of the specimen slides mounted on the tray 320. The transport carriage allows movement of the lifter heads left and right along the axis of the lead screw 381, while vertical position of each of the lifter heads is independently controlled by means of stepper motors such as 150 and 151 as shown in FIG. 1.

Figure 4:
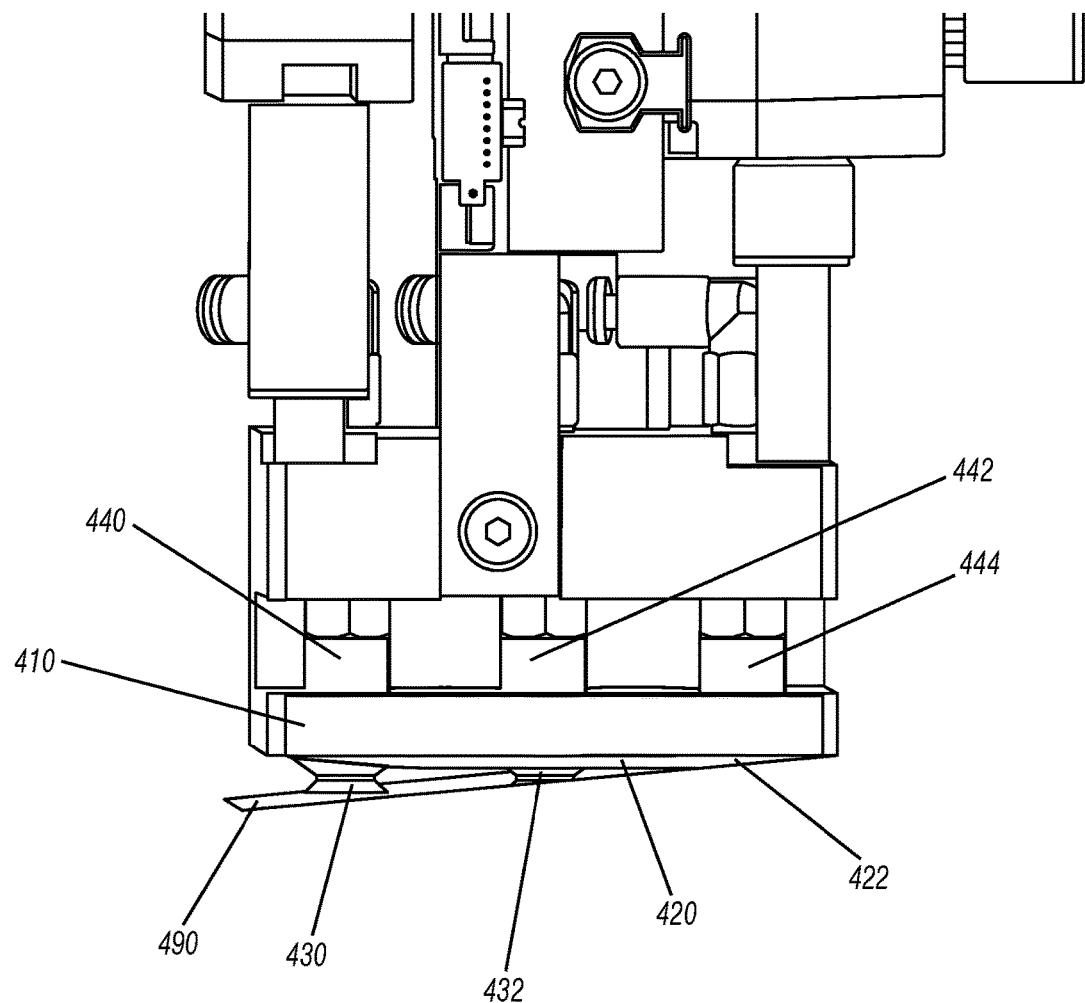
FIG. 4 depicts a perspective view of a lifter head 410 holding a single coverslip 490 in cantilever mode.

FIG. 4 shows lifter head 410 picking up a single coverslip 490 in cantilever mode. Gas conduits 440, 442 connect suction cups 430, 432, respectively, to a pneumatics module (not shown), while gas conduit 444 fluidly connects a suction cup hidden by coverslip 490. As explained elsewhere, the vacuum selectively applied at the suction cups 430, 432, and the hidden suction cup allow the coverslip 490 to be peeled from a stack of coverslips while avoiding or minimizing the accidental acquisition of more than one coverslip and while avoiding or minimizing the accidental breakage of the coverslip 490, in some embodiments. In this embodiment, the bottom surface 420 of lifter head 410 has chamfer 422 that facilitates the cantilever mode.

Figure 5:
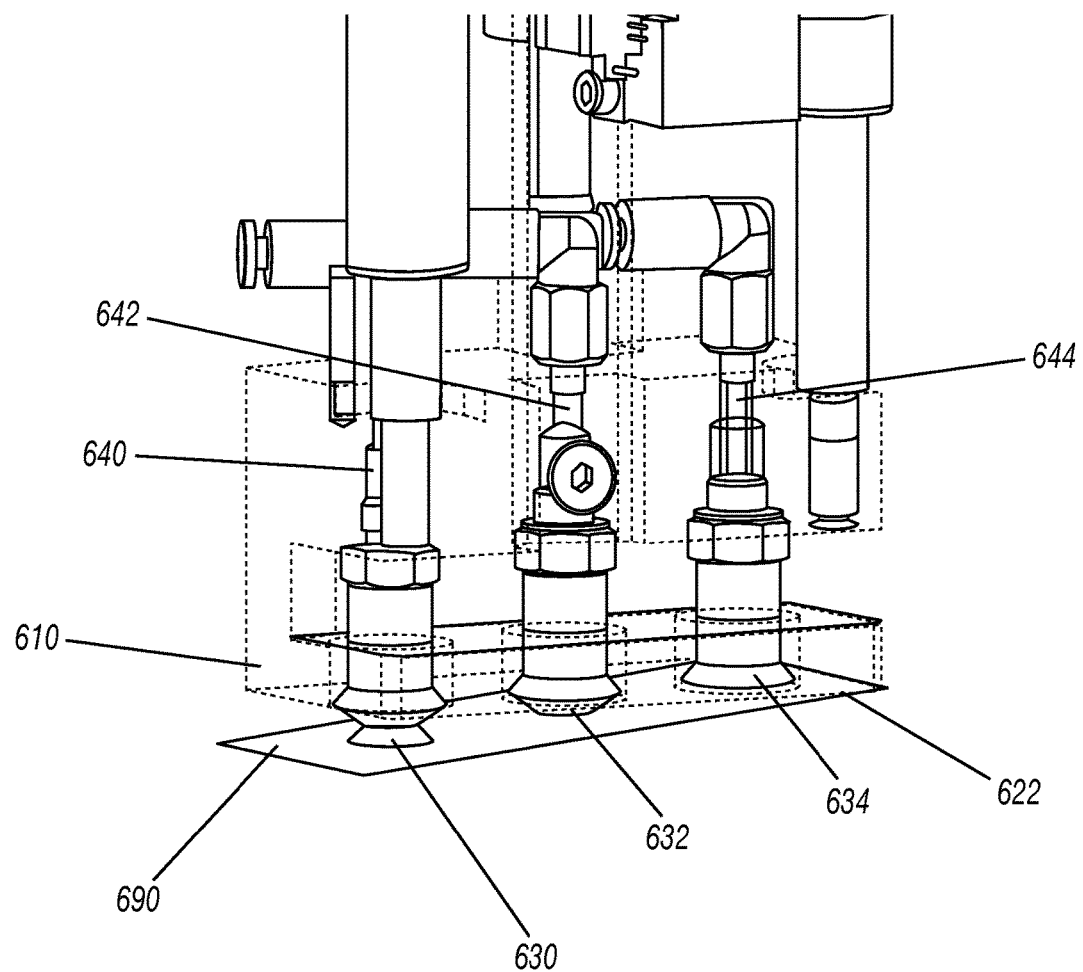
FIG. 5 depicts a perspective view of a lifter head 610 picking up a single coverslip 690, illustrating the internal pneumatic plumbing for the lifter head.

FIG. 5 shows a similar embodiment to that depicted in FIG. 4, in which lifter head 610 is rendered transparent. Suction cups 630, 632, 634 can be seen holding coverslip 690 in cantilever mode against chamfer 622. Also visible are the gas conduits 640, 642, 644 fluidly connecting suction cups 630, 632, 634 to the pneumatics module (not shown). As described elsewhere, the pneumatics module allows the selective application of vacuum, atmospheric pressure, or increase pressure at each of the suction cups 630, 632, 634 to control the selection, transport, and mounting of coverslip 690.

Figure 6:
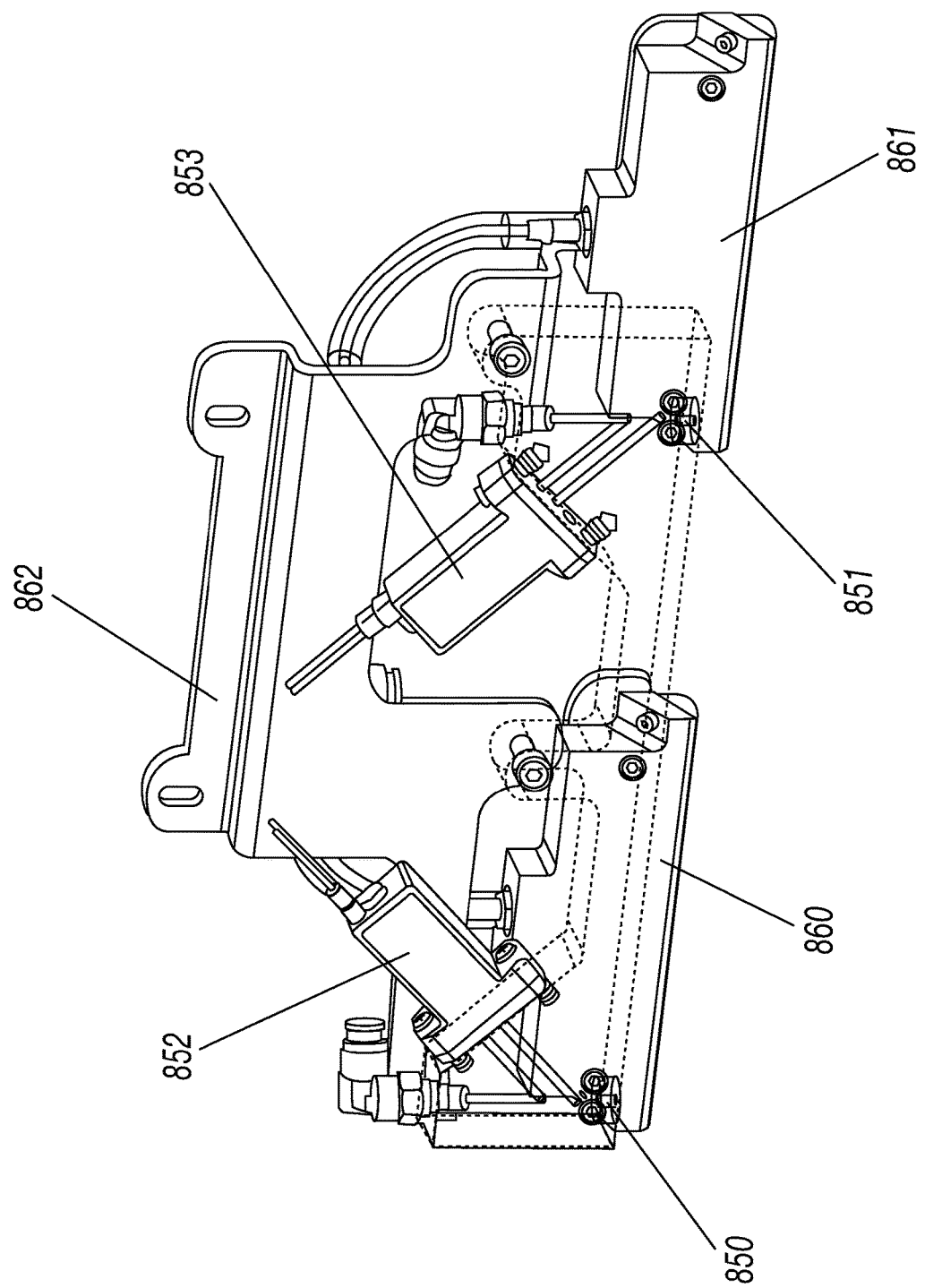
FIG. 6 depicts a perspective view of an assembly comprising fluid dispensers 850, 851 coupled to gas knives 860, 861 positioned over slides 888, 889.

FIG. 6 shows an assembly having fluid dispensers 850, 851 positioned with gas knives 860, 861. Fluid dispensers 850, 851 are fluidly connected to fluidics modules (not shown) which are mounted on bracket 862 to which are also mounted gas knives 860, 861. Bracket 862, in some embodiments, couples the fluid dispensers 850, 851 positioned with gas knives 860, 861 to a lifter head (not shown); while in other embodiments, the fluid dispensers 850, 851 and gas knives 860, 861 are associated with (not coupled to) a lifter head. In these other embodiments, fluid dispensers 850, 851 and gas knives 860, 861 can be manipulated independently of the lifter head. Optionally, for greater efficiency, the assembly can be configured to move in just one direction. In still other embodiments, more than one fluid dispenser is configured to deposit fluid on a slide, so that there is no need for side-to-side motion of assembly 700 if multiple fluid dispensers are configured for each slide. Or, the single point dispense can deposit fluid in a single spot at one end of the slide, from which point it is distributed by mechanism of the cantilevered coverslip vertical approach, as described elsewhere herein.

Figure 7:
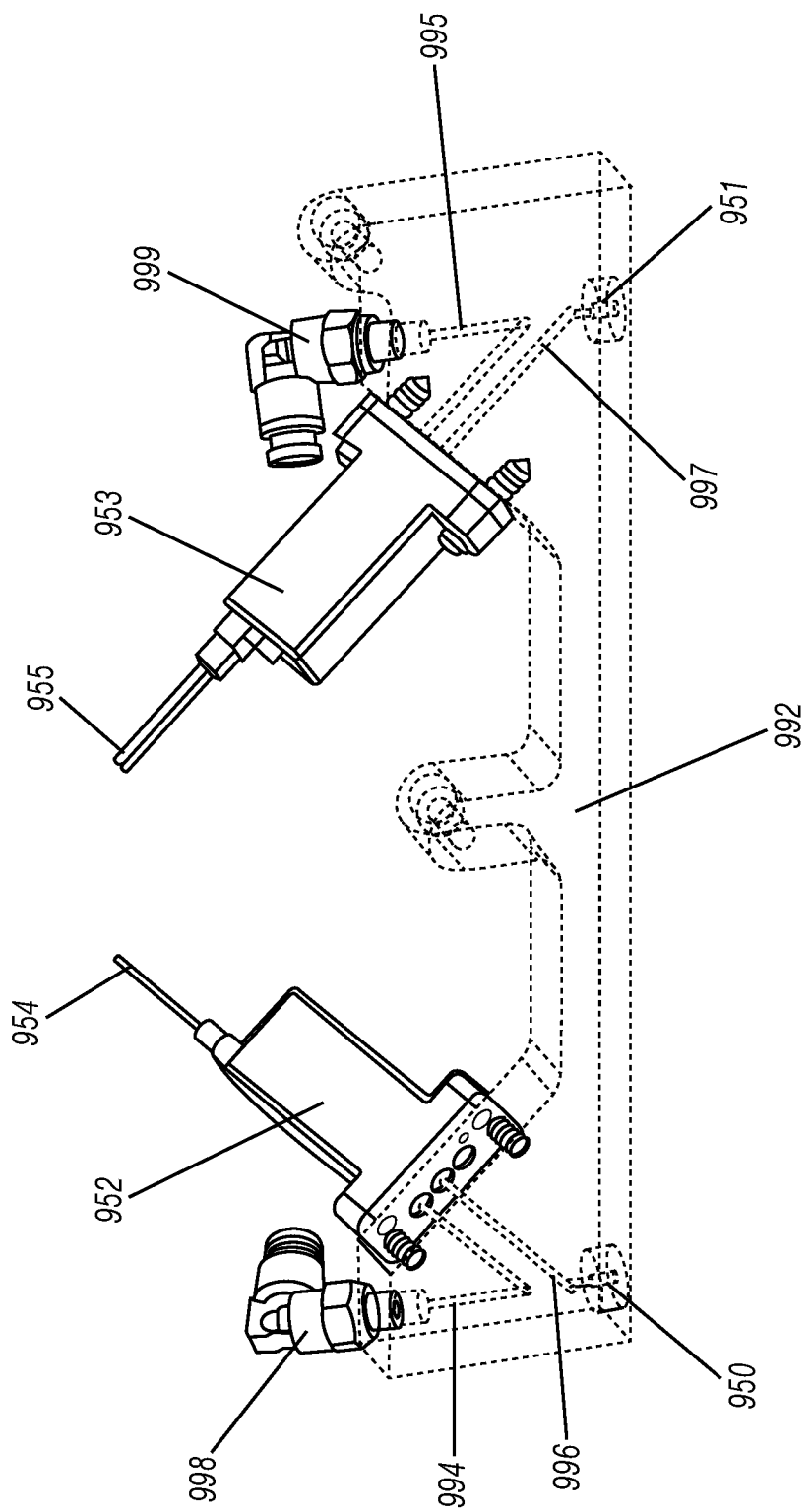
FIG. 7 depicts a perspective view of an embodiment comprising fluid dispensers 950, 951.

FIG. 7 shows an embodiment similar to that depicted in FIG. 6. Fluid dispensers 950, 951 are fluidly connected to fluid valves 952, 953, respectively, via fluid conduits 996, 997, respectively. Fluidics module 952 is fluidly connected to a fluid reservoir (not shown) via fluid conduit 994 and coupler 998. Fluidics module 953 is fluidly connected to a fluid reservoir (not shown) via fluid conduit 995 and coupler 999. Valves 952, 953 are kept in electronic communication to a control module (not shown) via wire sets 954, 955, respectively. Through that electronic communication, the control module controls the amount and the timing of fluid deposited by fluid dispensers 950, 951 onto the slide (not shown).

Figure 8:
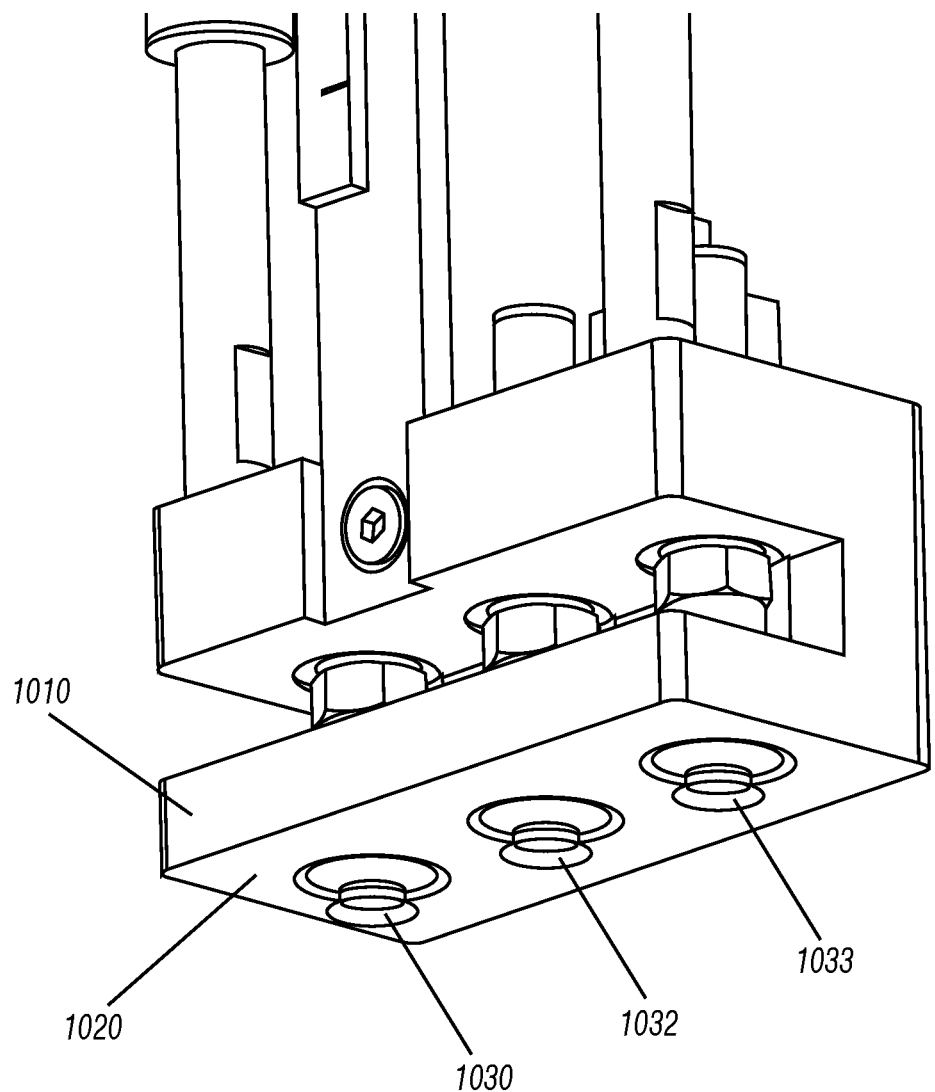
FIG. 8 depicts a perspective view of an embodiment comprising lifter head 1010 comprising a plate having a bottom surface 1020 that is substantially flat.

FIG. 8 depicts an embodiment comprising lifter head 1010 having suction cups 1030, 1032, 1033 extending from its bottom surface 1020. In this embodiment, bottom surface 1020 is substantially flat. Coverslips can be selectively and individually removed from a stack of coverslips by selective and sequential application of vacuum and pressure at suction cups 1030, 1032, 1033.

Figure 9:
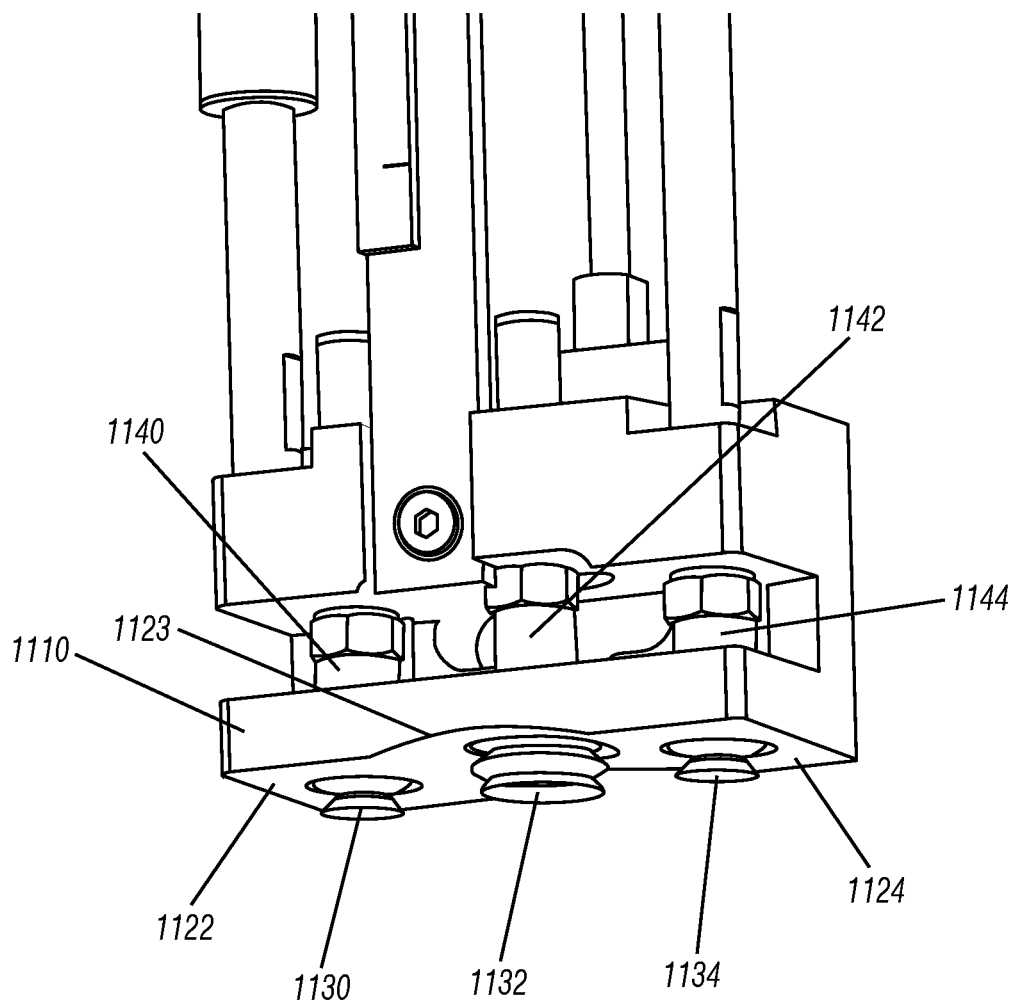
FIG. 9 depicts a perspective view of an embodiment comprising lifter head 1110 comprising a center concave configuration 1123 about suction cup 1132.

FIG. 9 depicts an embodiment that differs from that shown in FIG. 8 in that the bottom surface of lifter head 1110 features a center concave configuration 1123 flanked by substantially flat, substantially parallel surfaces 1122, 1124. Also, suction cup 1132 has a diameter larger than the diameters of suction cups 1130, 1134. Gas conduits 1140, 1142, and 1144 fluidly connect suction cups 1130, 1132, 1134, respectively, to a fluidics module (not shown). The center concave configuration 1123 is a concave feature about suction cup 1132 that aids in the selective removal of an individual coverslip, as will be shown in FIG. 10.

Figure 10:
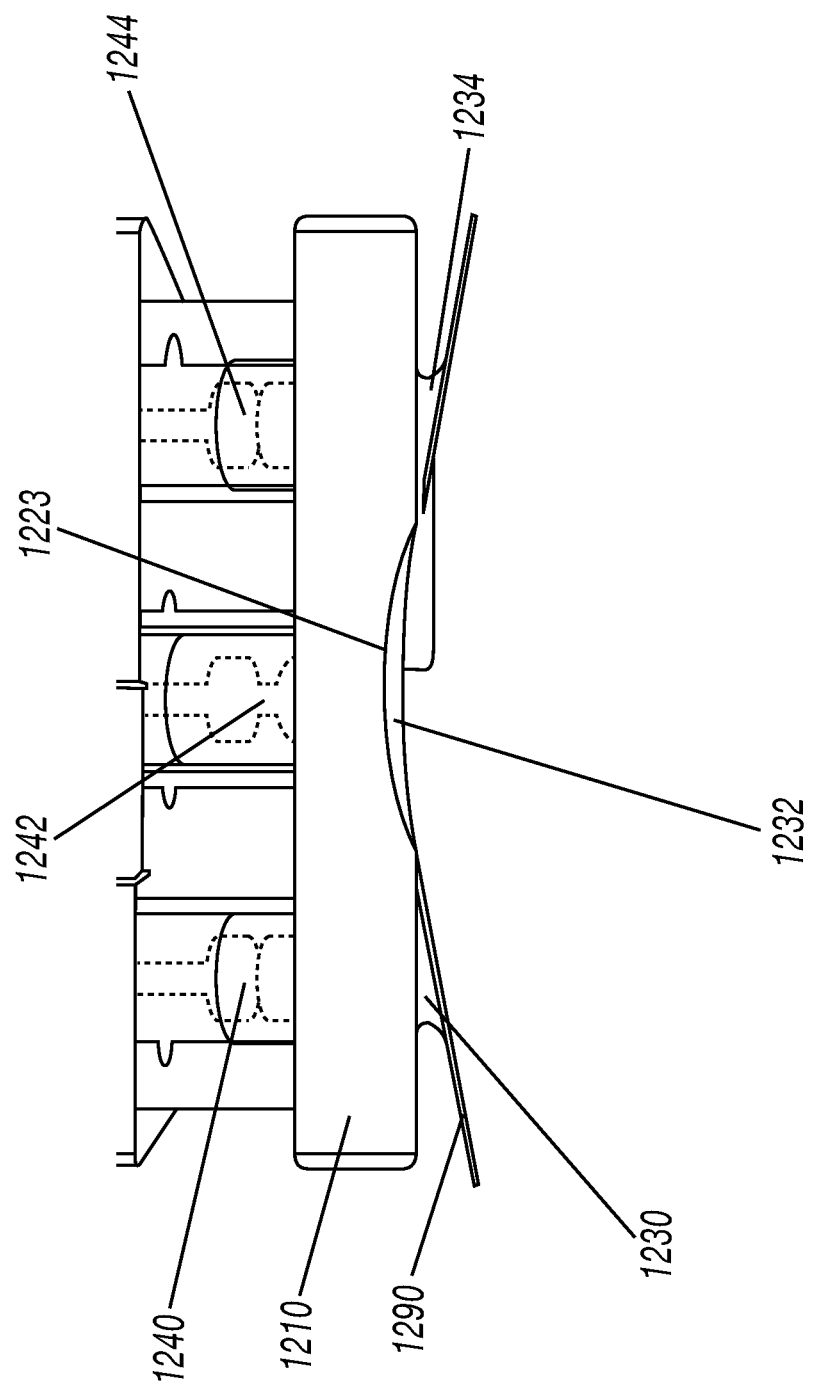
FIG. 10 depicts an embodiment of a lifter head 1210 comprising a center concave configuration 1223 while gripping a coverslip 1290.

FIG. 10 provides a photograph of an embodiment similar to that depicted in FIG. 9. Here, lifter head 1210 has suction cups 1230, 1232, 1234 extending from its bottom surface and gripping a coverslip 1290. The vacuum on suction cup 1232 causes the coverslip 1290 to conform to the concave shape of center concave configuration 1223. That concave shape encourages the coverslip 1290 to separate from the next adjacent coverslip in a stack of coverslips, thereby allowing lifter head 1210 to pick up one and only one coverslip 1290. The pressure at suction cups 1230, 1232, 1234 can be adjusted in any suitable sequence and in any suitable manner. For example, a vacuum can be drawn first at suction cup 1234 via gas conduit 1244, and then a stronger vacuum can be drawn at suction cup 1232 via gas conduit 1242, and finally a vacuum can be drawn at suction cup 1230 via gas conduit 1240. Or, a vacuum can be drawn simultaneously at suction cups 1230, 1232, 1234, if desired. Otherwise a vacuum can be applied to suction cup in the order 1232 to impart a "frown" shape to the retained coverslip.

Figure 11:
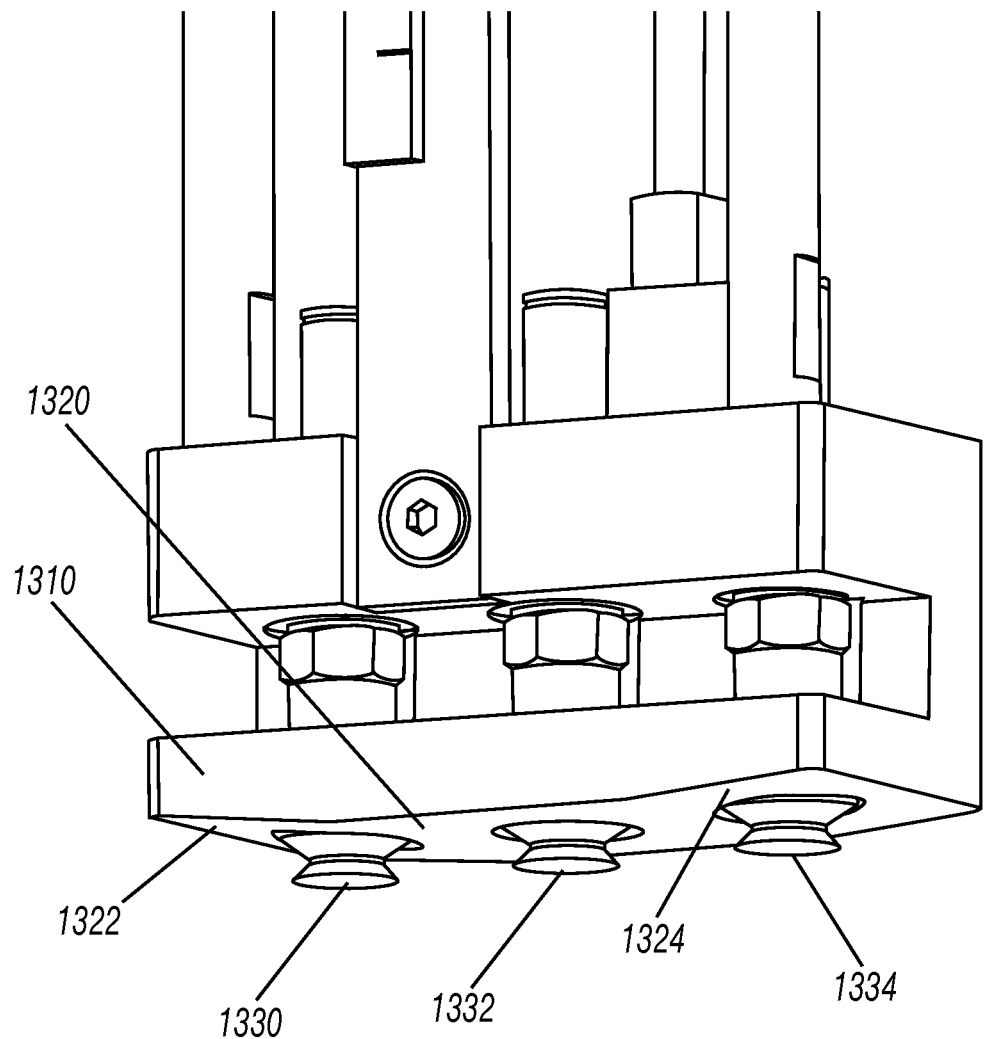
FIG. 11 depicts a perspective view of an embodiment comprising lifter head 1310 having a bottom surface 1320 featuring chamfers 1322, 1324.

FIG. 11 depicts an embodiment in which lifter head 1310 has a bottom surface 1320 featuring chamfers 1322, 1324. Those chamfers 1322, 1324 allow suction cups 1330, 1332, 1334 to reliably lift and separate a single coverslip from a stack of coverslips. In some cases, chamfers 1322, 1324 form an angle with bottom surface 1320. The angle can have any suitable magnitude, such as for example 1-30 degrees. Care should be taken so that the angle is not so great as to increase the risk of breaking the coverslip when suction cups 1330, 1332, 1334 apply a vacuum.

Figure 12:
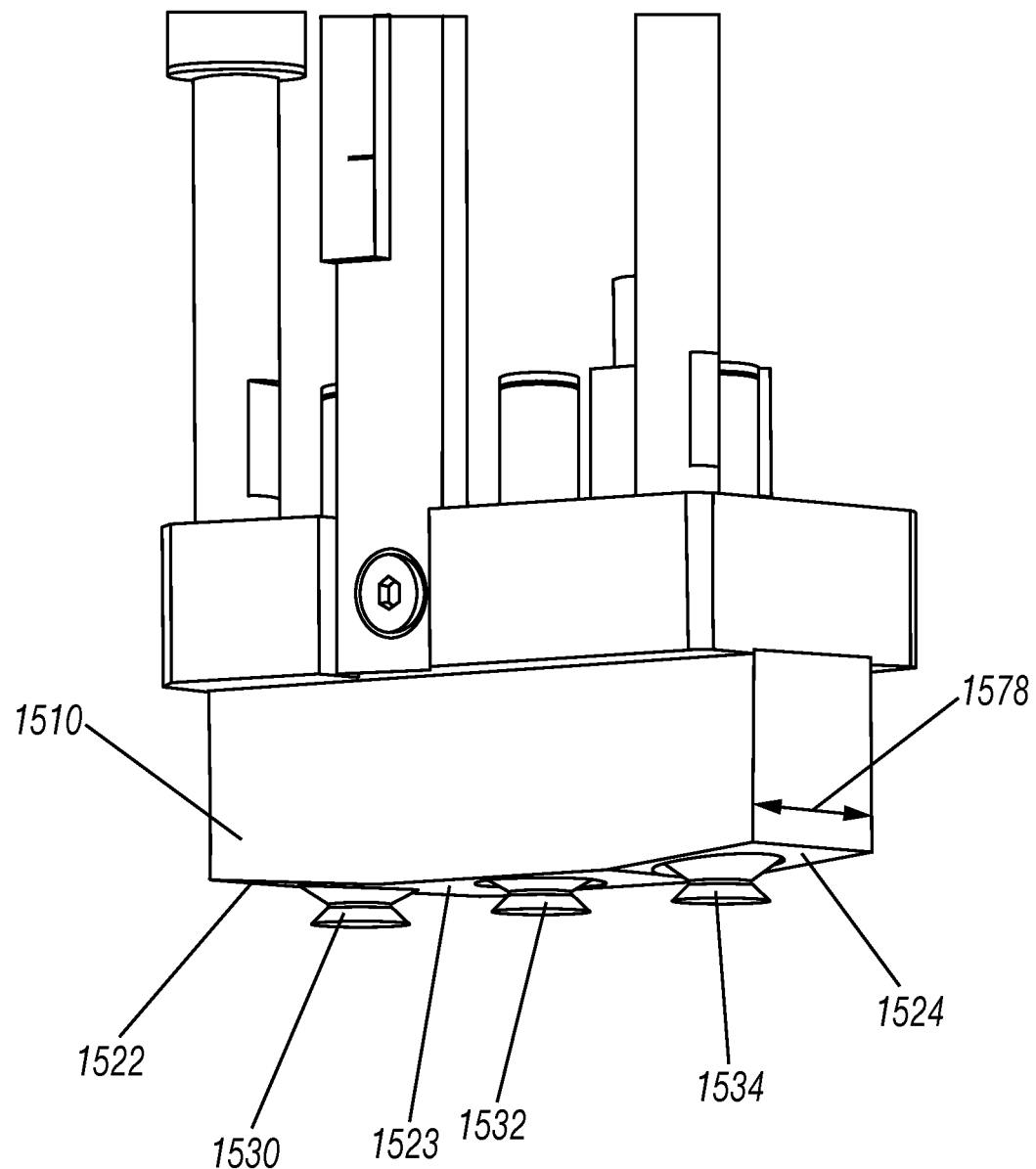
FIG. 12 depicts a perspective view of an embodiment comprising lifter head 1510 having chamfers 1522, 1524 and a width 1578 that is narrower than the width of a standard coverslip.

FIG. 12 provides a perspective view of a further embodiment in which lifter head 1510 has a width 1578 that is narrower than some other embodiments disclosed herein. A smaller width, it is believed, minimizes contact between the coverslip and the bottom surface of the lifter head 1510. If fluids are present, they can complicate coverslip mounting, because they will cause the coverslip to adhere to the lifter head 1510, and any fluid that adheres to the bottom of the lifter head has the potential to be transferred back to the stack of unused coverslips during a subsequent retrieval step, which can lead to coverslip adhesive sticking together. In this embodiment, bottom surface 1523 of lifter head 1510 has chamfers 1522, 1524 at the places where suction cups 1530, 1534 emerge. Suction cup 1532, in the center, emerges from substantially flat bottom surface 1523.

Figure 13:
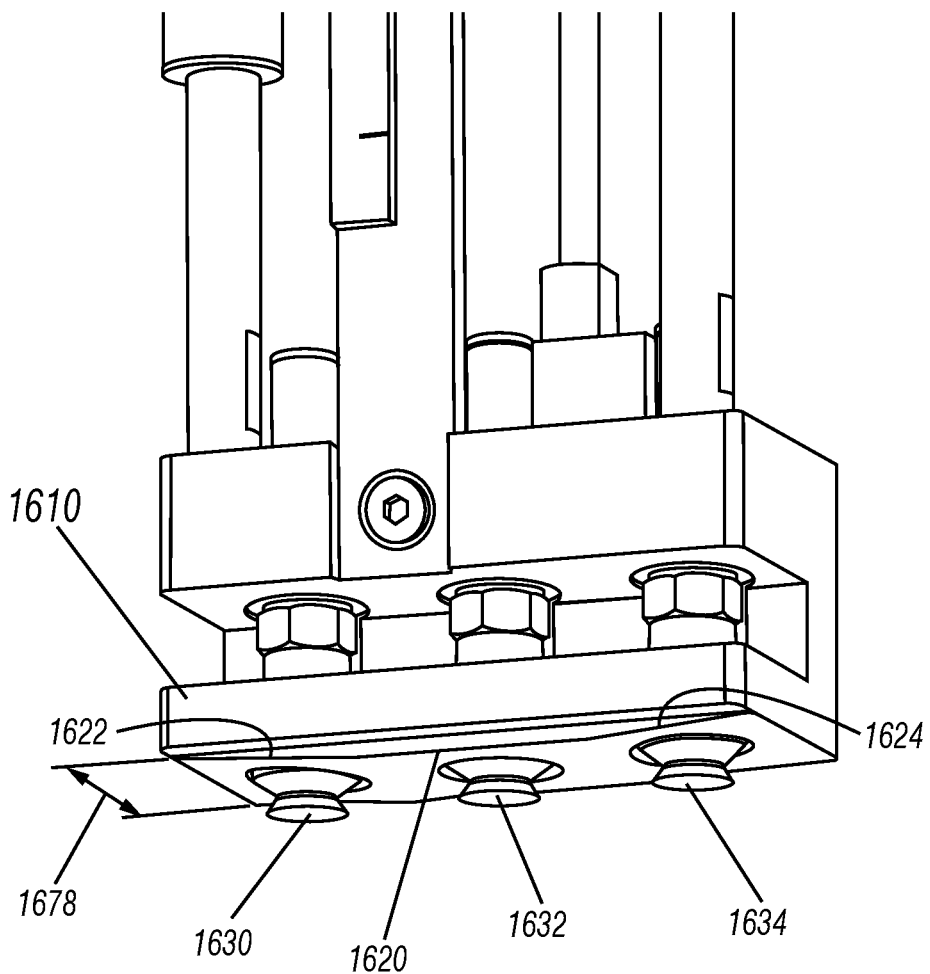
FIG. 13 depicts a perspective view of an embodiment comprising lifter head 1610 wherein a portion of the bottom surface 1620 has a width 1678 that is narrower than the width of a standard coverslip. This embodiment also features chamfers 1622, 1624.

FIG. 13 shows a further embodiment in which lifter head 1610 has a feature in its bottom surface 1620 having a width 1678 that is narrower than the main body of lifter head 1610. Feature includes chamfers 1622, 1624, about suction cups 1630, 1634, respectively. Suction cup 1632 emerges from the substantially flat bottom portion 1620.

Figure 14A:
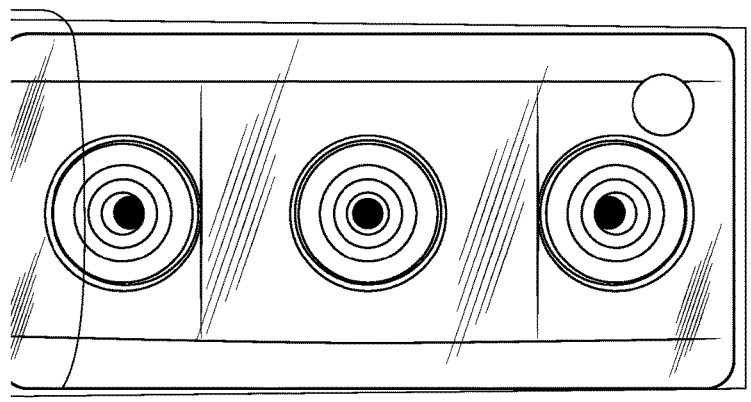
FIGS. 14 A-C depict one embodiment comprising lifter head 1710 mounting a coverslip 1790 on slide 1793, as viewed through the slide 1793 and further depicting the advance of a fluid meniscus as a coverslip (not seen) is laid down onto the slide.
Figure 14B:
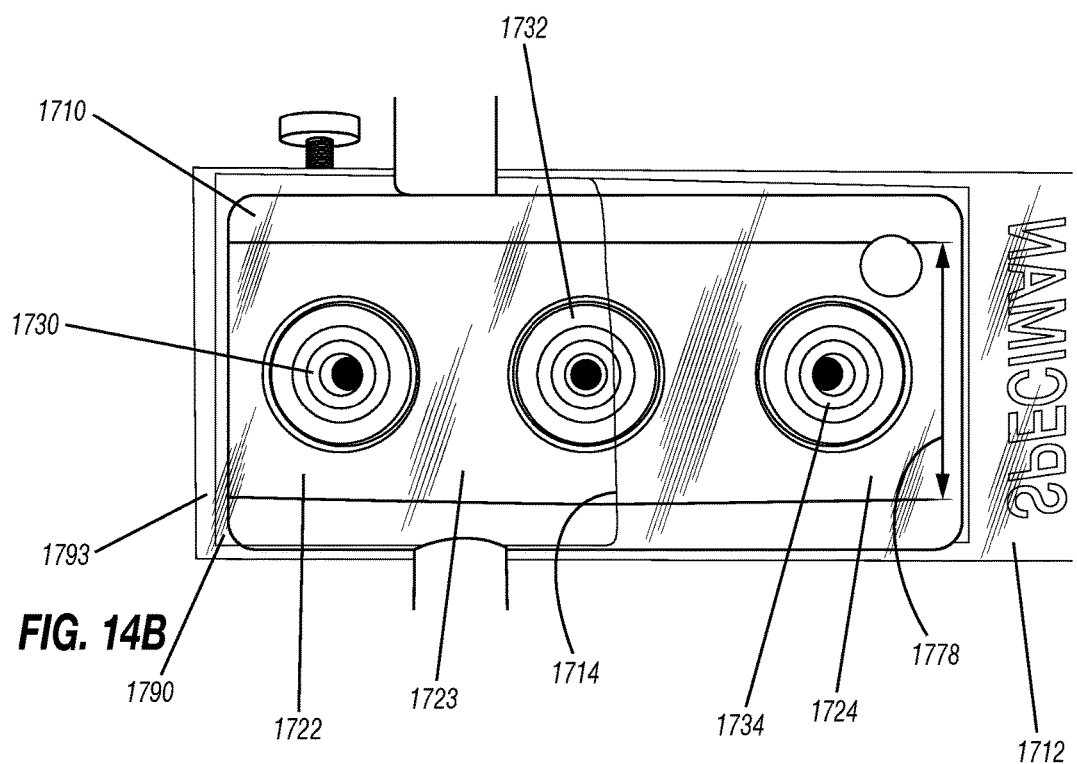
Figure 14C:
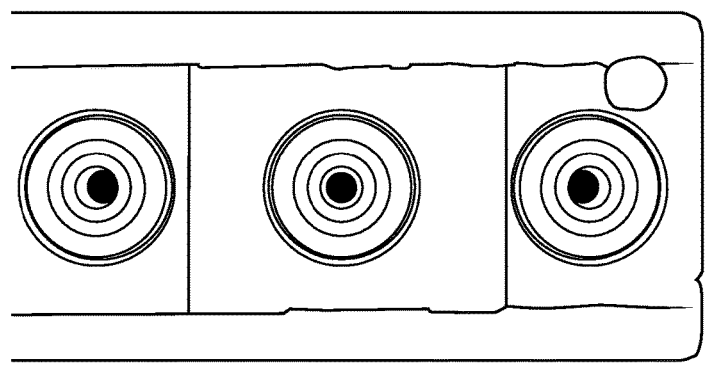
Figures 15A, 15B:
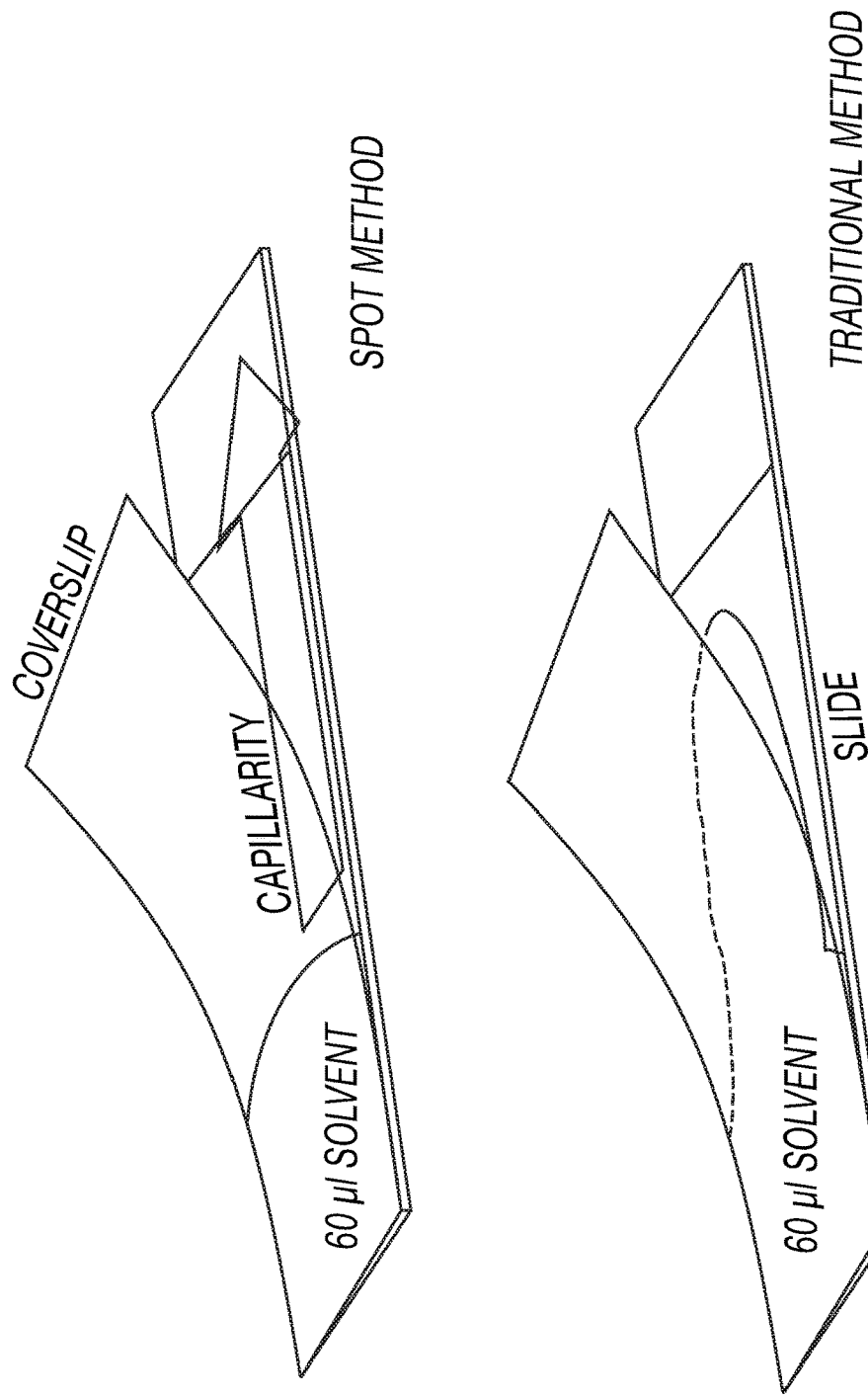
FIGS. 15 A-B depict an embodiment of a coverslip laydown having a volume of fluid placed at one particular spot the surface of a slide versus applying the same amount of fluid across the surface of the slide prior to laying down the coverslip.
Figure 16B:
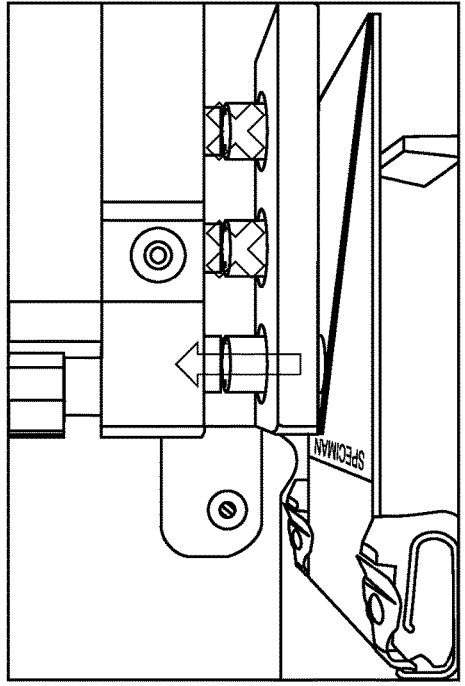
FIGS. 16 A-D depict a cantilevered coverslip laydown process by means of four sequential photographs.
Figure 16D:
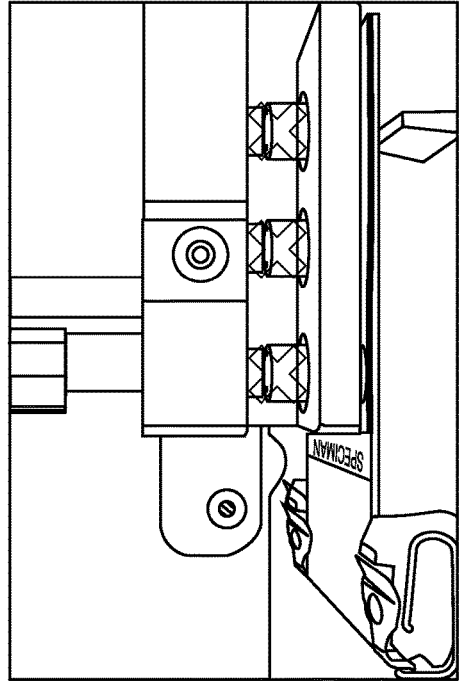
Figure 16A:
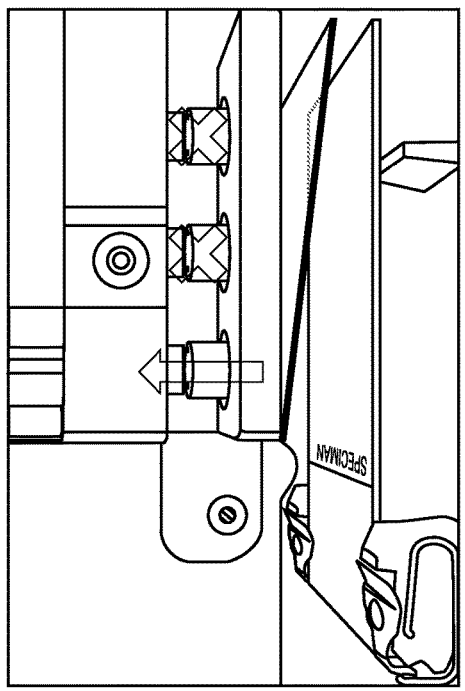
Figure 16C:
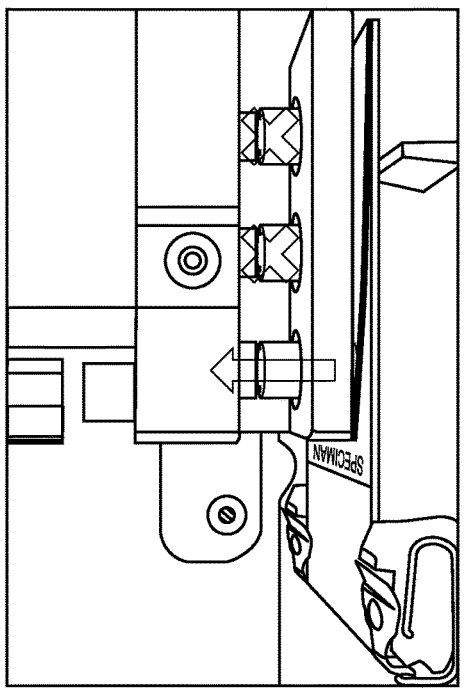

FIG. 14 shows a picture of an embodiment similar to that depicted in FIG. 13. Here, lifter head 1710 has engaged coverslip 1790 with suction cups 1730, 1732, 1734 to force the coverslip to conform to the geometry of the bottom surface of the lifter head 1710. That bottom surface features chamfer 1722, substantially flat portion 1723, and chamfer 1724. The bottom surface has a feature having a width 1778 that is narrower than the body of the lifter head 1710. FIG. 14 also shows the mounting of the coverslip 1790 to slide 1793, and as the coverslip 1790 connects, a line of fluid 1714 forms to indicate a bubble-free adherence of the coverslip 1790 to the slide 1793. In this case, coverslip 1790 is being mounted from the distal end of slide 1793 toward the label end 1712 of slide 1793.

FIG. 15 A depicts an embodiment of the invention where in the placement of 60 μL of fluid near one end of the slide results in a controlled movement of the fluid as the coverslip is placed on the slide. This laydown process creates a capillary wavefront that is controlled by slide edges and the coverslip. FIG. 15 B depicts a situation where the fluid is more widely dispensed resulting in a "wet" slide surface. As the coverslip is lowered across the slide the wet puddle of fluid is difficult to control, resulting in over spill or longer times to place the cover slip or entrapment of bubbles. The inventors have shown that the wet process can result produce merging wave fronts from premature contact and bubble from static discharges from the flexed or bent coverslip. The "dry" surface process shown in FIG. 15 A tends to produce a single wave front and creates no electrical ground for any static electricity built up in the coverslip. This results in less production or capturing of bubbles under the coverslip.

FIG. 16 shows, by a series of pictures, a method of mounting the coverslip on a slide. First, a gas knife (not shown) blows off the slide having a biological specimen thereon. Next, fluids are deposited by fluid dispensers onto the slide, and excess fluid is removed by the gas knife (not shown). Then the lifter head selects an individual coverslip and carefully places it on the slide, using a cantilever mode to accomplish a bubble free mounting. Finally, lifter head releases the mounted coverslip.

Figure 18:
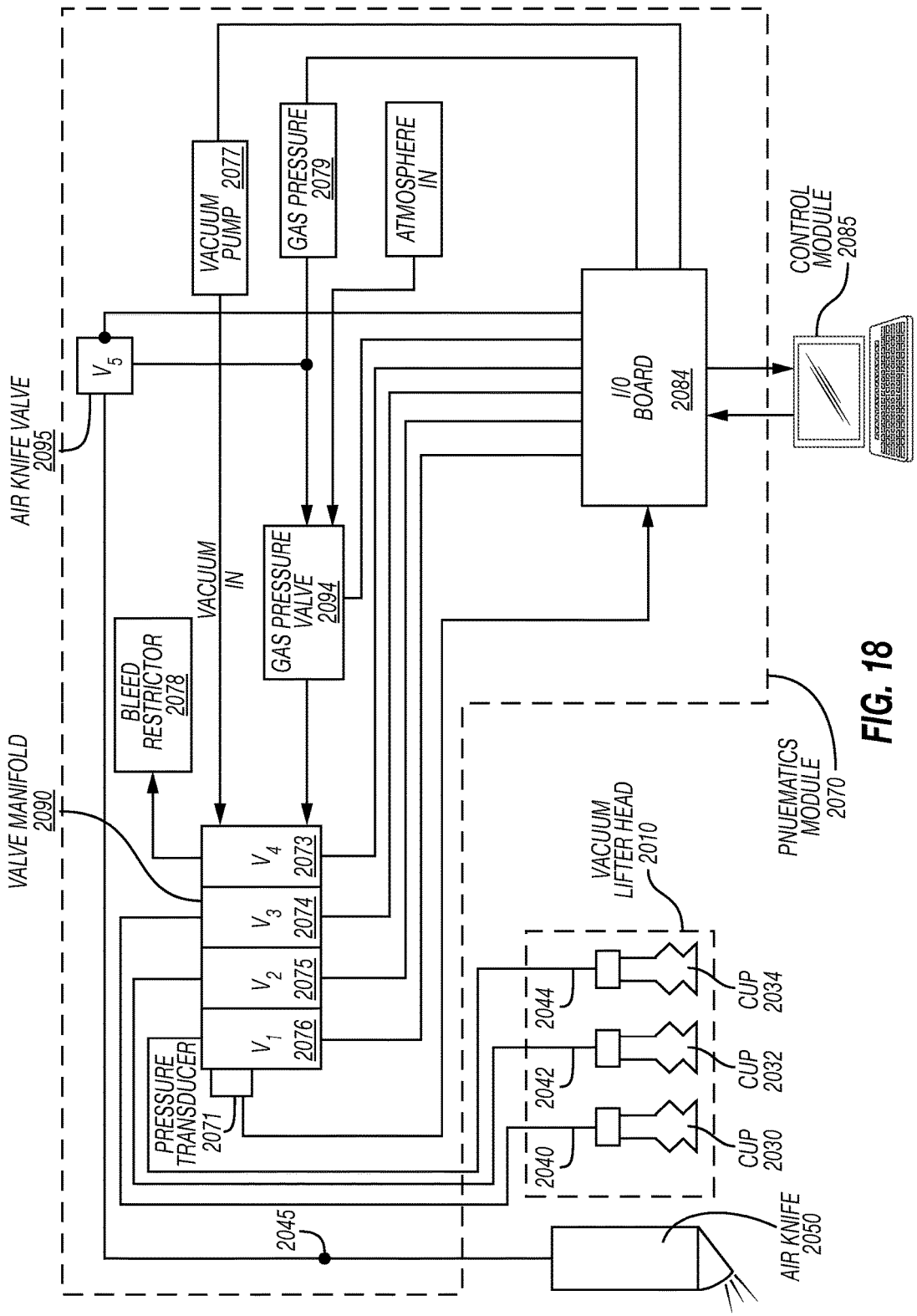
FIG. 18 depicts schematically an embodiment showing the relationship between lifter head 2010, pneumatics module 2070, and control module 2085.

FIG. 18 shows schematically the relationship between lifter head 2010, pneumatics module 2070, and control module 2085. Lifter head 2010 has suction cups 2030, 2032, 2034 extending from its bottom surface. Those suction cups 2030, 2032, 2034 are in fluid communication with the pneumatics module 2070 via gas conduits 2040, 2042, 2044, respectively. The pneumatics module 2070 provides sensor 207 land control valves 2074, 2075, 2076 for each gas conduit 2040, 2042, 2044, respectively. Each control valve 2074, 2075, 2076 is in electronic communication and is controlled by the control module 2085. Sensor 2071 is a vacuum pressure transducer also in electronic communication with the control module 2085 through the digital TO board 2084, so the control module 2085 can determine whether a coverslip has properly adhered to the suction cups 2030, 2032, 2034, or if the coverslip has broken. A fourth control valve, 2073, opens and closes the vacuum manifold side of valve manifold 2090, thereby bleeding the vacuum through bleed restrictor 2078. This function is useful for performing a slow release of vacuum pressure during the coverslip laydown step. The air knife 2050 is connected by means of gas conduit 2045 to air knife valve 2095, which is controlled by the control module 2085 through the digital TO board 2084, to allow pressurized gas to exit through the air knife In addition, the pneumatics module 2070 also contains or is fluidly connected to a vacuum source 2077, and optionally a gas source 2079. In some cases, the gas is air.

Figure 19:
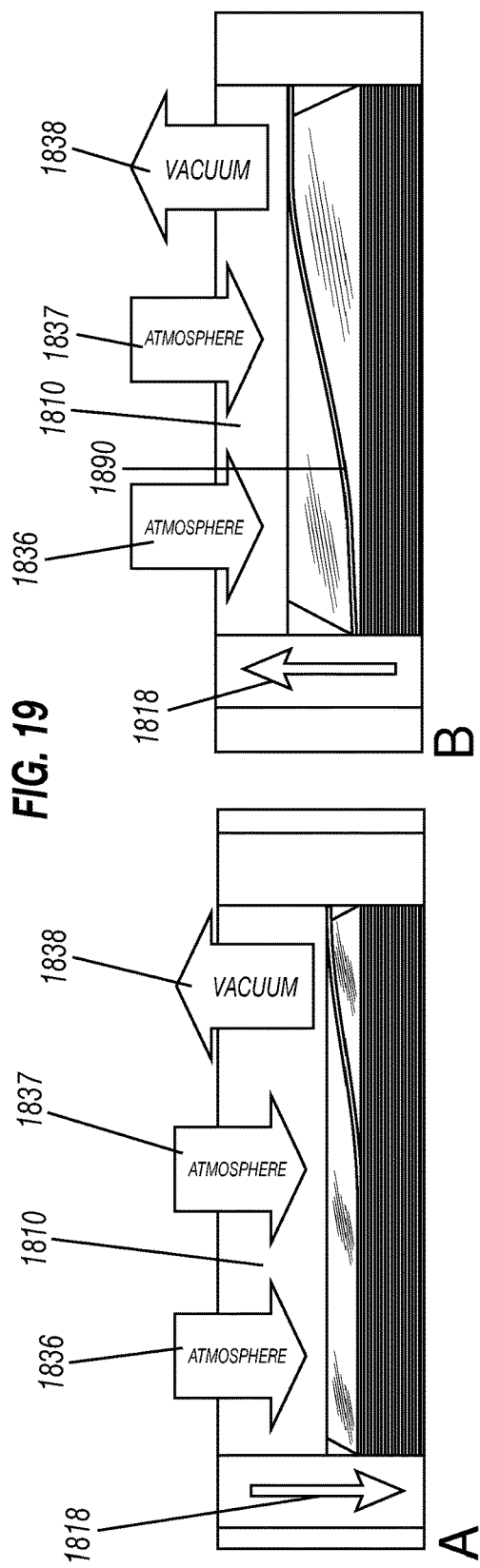
FIG. 19 depicts by way of multiple drawings one method for lifter head 1810 to select one coverslip 1890 from a stack of coverslips 1892.
Figure 19:
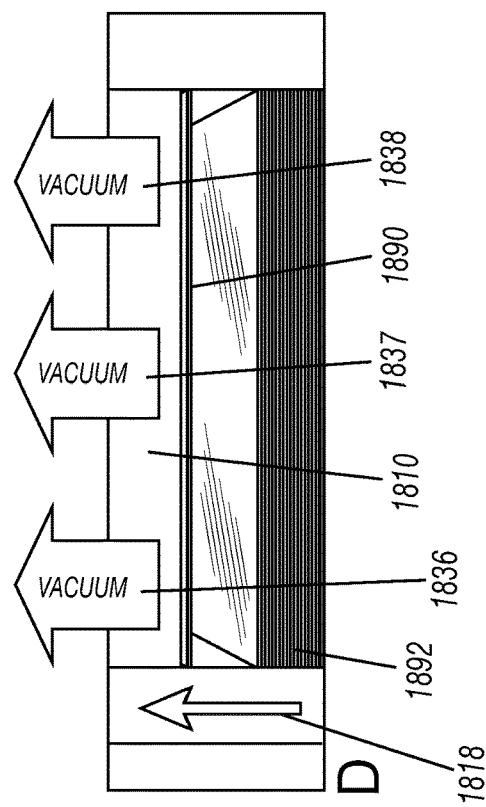
Figure 19:
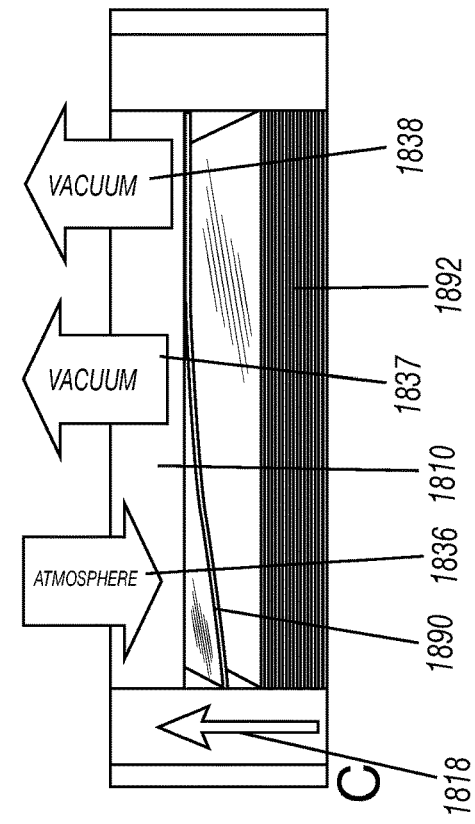

FIG. 19 depicts by photographs one method for selecting an individual coverslip 1890 from a stack of coverslips 1892. In FIG. 19 A, the right-hand suction cup (not visible) has a vacuum 1838 drawn on it, while the remaining two suction cups are held at atmospheric pressure 1836, 1837. Lifter head 1810 is moved down 1818 toward a stack of coverslips 1892, where the vacuum 1838 engages the top coverslip 1890. In FIG. 19 B, lifter head 1810 is moved upward 1818, lifting coverslip 1890 from a stack of coverslips 1892. In FIG. 19 C, two suction cups now have vacuum 1837, 1838 drawn on them, separating coverslip 1890. In FIG. 19 D, all three suction cups have vacuum: 1836, 1837, 1838. Accordingly, coverslip 1890 conforms to the geometry of the bottom surface of lifter head 1810.

At least one embodiment relates to an automated coverslipper for mounting a coverslip on a slide, comprising: (i) at least one coverslip; (ii) at least one slide containing a biological specimen; and (iii) at least one lifter head comprising a plate having a bottom surface with at least three individually controlled suction cups arranged thereon, each suction cup being fluidly connected, by way of a gas conduit, to a pneumatics module, which includes a vacuum source, a sensor, and a control-valve for each plumbed gas conduit, the pneumatics module being configured to supply an independent vacuum or pressurized gas to each the suction cup to enable the lifter head bottom surface to perform a cantilever pickup of the coverslip and a cantilever laydown of the coverslip on the slide, or to provide one or more mechanized pulsed movements, or to apply one or more pressurized air bursts.

In one embodiment, the coverslipper further comprises: (i) a transporter coupled to a motor and attached to the lifter head in a manner thereby suspending the lifter head in a substantially vertical position, and configured to move the lifter head horizontally, vertically, or diagonally to position the bottom surface of the lifter head over the coverslip during retrieval or over the slide during laydown; and (ii) a control module in electrical communication with the transporter, the lifter head, the suction cups, and the pneumatics module, wherein the control module coordinates function of components of the coverslipper. In one embodiment, the coverslipper further comprises: (i) at least one fluid dispenser coupled to the lifter head and in fluid communication with a fluidics module that supplies a reagent, such as glue or a glue solvent to the fluid dispenser and is configured to dispense fluid on the slide; and (ii) at least one gas knife coupled to the lifter head and in fluid communication with a pneumatics module and is configured to provide gas to the upper, specimen-bearing surface of the slide; wherein the fluid dispenser and the gas knife are suspended in a substantially vertical position and the lifter head is configured to horizontally move the fluid dispenser and the gas knife over the slide, and the fluid dispenser and the gas knife, are in electrical communication with the control module. In a further embodiment, the coverslipper further comprises: (i) at least one slide tray holding, in a substantially horizontal position, a plurality of the slides arranged in one or more rows; and (ii) a cartridge containing a plurality of the coverslips vertically stacked and arranged so the top of the stack is accessible via a top opening in the cartridge. In a further embodiment, the cartridge and stack of coverslips are configured so the stack inside the cartridge is tilted at one or more angles.

In another embodiment, the coverslipper has two lifter heads positioned in tandem to work simultaneously or independently on two rows of slides.

In a further embodiment, the present disclosure relates to an apparatus and method for performing a cantilever pick up of a coverslip. In this embodiment, the lifter head is configured to provide independent vacuums to the three suction cups to perform the cantilever pick up of the coverslip from the cartridge to thereby pick up and hold the coverslip to the lifter head's bottom surface. In this manner, the lifter head is configured with three suction cups and the vacuum source can be activated in a manner to provide an independent vacuum to each of the three suction cups to thereby lift up and hold one end only of the coverslip to the bottom surface of the lifter head and thereby lift away the coverslip from the cartridge during cantilever pickup. In this manner, during cantilever pickup, the lifter head is configured to rise up and lift away the coverslip being held at one end only to the bottom surface of the lifter head and thereby lift away the coverslip from the cartridge. Then the lifter head is configured to activate the vacuum source and provide, either simultaneously or sequentially, an independent vacuum to the remaining two suction cups to thereby hold the entire coverslip to the bottom surface of the lifter head. The lifter head then transports and positions the suctioned coverslip over the slide.

In one embodiment, the lifter head further comprises one or more vacuum sensors to measure vacuum pressure on the suction cups at one or more times.

In a further embodiment, the disclosure relates to a method for performing a cantilever laydown of the suction lifted coverslip. This cantilever laydown comprises laying down the lifted coverslip one end at a time on the slide by gradually bleeding off the vacuum in the three suction cups one at a time. In this manner, one end of the coverslip (the end without suction) is first laid onto the slide and the remainder of the coverslip (under suction and held to the lifter head) is later rolled down onto the slide when the remaining vacuum is gradually bled off. In one embodiment, the lifter head is configured to perform a cantilever laydown by first removing the vacuum of two adjacent suction cups so that only one suction cup has a vacuum. The sole suction cup under suction holds one end of the coverslip and the other end of the coverslip is then lowered and laid onto the slide and then vacuum is gradually removed on the last suction cup so that the remainder of the coverslip is then rolled down onto the slide.

The present disclosure also relates to a method for performing a cantilever pick up of a coverslip from a coverslip cartridge, comprising: (i) positioning at least one lifter head comprising a plate having a bottom surface with at least three individually controlled suction cups arranged thereon over a topmost coverslip in the cartridge, wherein each the suction cup is fluidly connected, by way of a gas conduit, to a pneumatics module, which includes a vacuum source, a sensor, and a control-valve for each gas conduit, the pneumatics module is configured to supply an independent vacuum or pressurized gas to each of the suction cup; (ii) activating the vacuum source in one of the three suction cups to thereby lift up and hold one end only of the topmost coverslip to the bottom surface of the lifter head; (iii) raising the lifter head holding the lifted end of the coverslip; (iv) activating the vacuum source in the remaining suction cups, either simultaneously or sequentially, to further suction and lift up so the three suction cups maintain a vacuum and completely lift and hold the coverslip to the bottom surface of the lifter head. In this method the lifter head is configured so that the cantilever pick up induces a curvature on the coverslip that aids in separating the suctioned coverslip from other coverslips in the cartridge.

The present disclosure also relates to a method for performing a cantilever laydown of a coverslip on a specimen-bearing microscope slide, the method comprising: (i) positioning a suction lifted coverslip over the slide, wherein the suction lifted coverslip is held to a bottom surface of a lifter head by a vacuum in three individually controlled suction cups arranged on the bottom surface, wherein each the suction cup is fluidly connected, by way of a gas conduit, to a pneumatics module, which includes a vacuum source, a sensor, and a control-valve for each gas conduit, and the pneumatics module is supplying an independent vacuum to each of the three suction cups thereby holding the coverslip to the bottom surface; and (ii) gradually removing the vacuum the three suction cups so one end of the coverslip is first laid onto the slide and the remainder of the coverslip is then rolled down onto the slide. In one embodiment, the method comprises first removing the vacuum in two of the suction cups so the coverslip is held at one end only by the one suction cup that still has a vacuum. In a further embodiment, the method comprises utilizing one or more mechanically pulsed movements to slowly lower the coverslip onto the slide. In yet another embodiment, the method comprises applying one or more bursts of deionized air through the suction cups to further discourage static events and to squeeze out remaining excess fluid.

Referring now to the figures, FIG. 1 depicts an embodiment illustrating an assembly plate 100 carrying two lifter heads 110 and 111 each with three suction cups 130, 132, 134, 131, 133 and 135, and each employing a vertical axis stepper motor, stabilized by 2 linear roller bearings supporting vertical movement of each lifter head. The U-shaped brackets mounted on the top of each assembly are optical home flag sensors configured to detect when the lifter head has reached the high end of its travel. The vertical linear strip attached mid-plane to the front of the lifter on the left and to the rear of the lifter on the right has a magnetic strip encoder to provide a signal corresponding to the lifter head distance from the home sensor in the vertical direction.

The coverslipper is configured so each lifter head has three individually plumbed suction cups in fluid communication with a pneumatics module with control valves, and sensors. The pneumatics module supplies an independent and controllable vacuum or pressurized gas to each individually plumbed suction cup to perform a cantilever pickup of a single coverslip from the cartridge (i.e., lifts and picks up one end of the coverslip first and then lifts and picks up remainder of the coverslip) and to perform a cantilever laydown of the coverslip on the slide (i.e., lays down one end of the coverslip first and then the remainder of the coverslip), or to apply air bursts.

In some embodiments, the automated coverslipper further comprises: (i) at least one fluid dispenser associated with the lifter head and in fluid communication with a fluidics module that supplies a reagent to the fluid dispenser; and (ii) at least one air knife associated with the lifter head and in fluid communication with a pneumatics module. In the coverslipper, one or more transporters coupled to a motor are attached to the lifter head. One such transporter is coupled to a motor and runs along an overhead rail and suspends the lifter head in a substantially vertical position, and is configured to horizontally and vertically move and position the lifter head so the bottom surface can pick up a coverslip from a cartridge and lay it down on a slide. The coverslipper also includes a control module in electrical communication with the first transporter, the lifter head, the suctions heads, and the pneumatics module, and is configured to coordinate function of components of the apparatus during operation.

Lifter Head Assembly—Referring to the Figures, the coverslipper of the present disclosure contains one or more lifter heads 110, 111, each configured to pick up and transport a single coverslip and lay it down on a specimen-bearing slide. Each lifter head includes a housing or plate having a bottom surface and at least three individually controlled suction cups, each in fluidic communication with a vacuum source. The lifter head may also be coupled or integrated with an air knife, fluid dispensers, and sensors.

In some embodiments, the suction cups can be circular, substantially circular or oval in shape, or they may have any other suitable shape capable of maintaining a vacuum to pick up and hold a coverslip. Vendors do offer non-circular suction cups, most useful would be the elongated oval shape. Such a shape could have the advantage of having a flex axis with low resistance to flexure, but the drawback is that the cup would then need to be aligned in a preferred direction, thereby complicating assembly of the device.

Referring to FIG. 11, in one embodiment, the suction cup is circular having a working face that is a curved surface with an inlet port in the center (See FIGS. 14 A-C). Each suction cup is attached to the bottom of the housing/plate and is accessible to the outside bottom surface to thereby maintain suction on a coverslip. Each suction cup can be configured to be flush with the bottom outside surface, be slightly recessed in a hole in the bottom surface, extend out for a short distance from the bottom surface, or be configured to extend out and recess back in a hole on the bottom surface.

The suction cup can be of any size or dimension capable of maintaining suction and picking up and holding a coverslip when vacuum is applied. In one embodiment, the suction cup is a suction cup having a diameter in a range of about 2 mm to about 20 mm, from about 3 mm to about 10 mm, from about 4 mm to about 8 mm, and in one embodiment is about 6 mm. In some embodiments, larger cups are may be use because they may provide greater force for the same vacuum, but they also require a physically larger apparatus, which can be undesirable, and there is a limit to the maximum diameter that is based on the geometry of the coverslip and the number of suction cups desired. For three cups in a straight line on a 2 inch (50.8 mm) long coverslip, the practical limit is about 10-12 mm diameter. The inlet port in the center working face of the suction cup is a circular opening with a maximum width in a range of about 5 mm to about 22 mm.

In some embodiments, the suction cups on a lifter head are identical in size and shape, or alternatively, they may vary in size and shape. The suction cups are made from any material suitable to supply and maintain a vacuum suction on a coverslip. For instance, the suction cups can be made from silicone, rubber, NBR, Urethane, plastic, etc. In one embodiment, the heads are vacuum suction cups made of silicone rubber. For example, the suction cups can be the silicone rubber vertical entry suction pads from SMC Corporation, part no. ZPT06BS-A5 having a 6 mm pad diameter.

As shown in FIG. 9, the lifter head housing/plate can have a one-piece construction or a multi-piece construction and can couple an individual gas line or conduit line 1140, 1142 and 1144, to each suction cup 1130, 1132, and 1134. Each line can include, without limitation, one or more conduits (e.g., hoses), valves, or other fluid components for establishing a fluidic connection between suction cup on the bottom surface plate and the pneumatic/pressurization device, which may also include on or more sensor(s) or a control valve. In one embodiment, each suction cup is fluidly connected to a conduit gas line that travels through, or along, the lifter head housing/plate to a pneumatic module that acts as a vacuum source. In this regard, a separate pneumatics module is connected to lifter head, so each head can be operated and controlled independently of the heads to supply an independent vacuum or pressurized air. As shown in FIG. 18 each pneumatics module comprises at least a conduit gas line, a sensor, a control-valve, and a pressurization and vacuum source (or a combine pressure and vacuum source), in fluid communication with a control valve for each individual suction cup. The vacuum device can draw a sufficient vacuum to securely pick up/lift and hold coverslip to the bottom outside surface of lifter head. The control valve can turn the vacuum on or off or apply a pressure volume of gas there through. It can also act as (or include) a bleeder valve to allow for a gradual transition from full vacuum to full release. Each suction cup can be turned to ambient suction or pressure, and actual settings may vary from cup to cup depending on the desired outcome. In general, vacuum device can draw a vacuum sufficient to pick up and hold a coverslip to the bottom surface of the lifter head. In some embodiments, the vacuum device is configured to produce a vacuum level in a range of about −7.2 psi to about −10 or more psi. The operation of the vacuum source can be adjusted achieve such vacuum levels or other desired vacuum levels. To release the suctioned coverslip, the vacuum can be eliminated or reduced. In this regard, the sensor and control valve can measure and change vacuum or air pressure, as needed. For instance, during the laydown process, the system is configured to slowly bleed off vacuum pressure to allow a controlled and soft cantilever laydown of a coverslip on a slide to reduce the "slap" of the released coverslip end with can produce bubbles in the fluid. This vacuum bleed can provide a gentle release of end of the coverslip being held or otherwise retained by one of the end suction cups. In one embodiment this valve has an orifice of about 0.7 mm. The process of lowering a coverslip onto the slide can take about 15 seconds per slide, and is dependent upon many factors, including desired coverslipper throughput. Pressurization device can include, without limitation, one or more vacuum devices, pumps, hoses, sensors, or the like to produce a pressure level up to about 25 psi. In one embodiment separate vacuum and pressure devices are utilized.

The pneumatic module further includes one or more pressure sensors to measure vacuum pressure during operation of the coverslipper. The sensor measures vacuum pressure when a coverslip is suctioned to the lifter head to determine the integrity of the coverslip (whether there are any broken or chipped coverslips) and to detect if more than one coverslip has been suctioned up to the bottom surface of the lifter.

In one embodiment, referring to FIG. 8, lifter head 1010 has the three individually plumbed circular suction cup heads 1030, 1032, 1033 arranged one after the other in a substantially straight line along the bottom surface. The suction cup heads are individually plumbed and controlled so each cup can work independently. Referring to FIG. 9, in some embodiments, the second of the three suction cup heads, i.e., the central suction cup 1132, is larger (larger diameter) relative to the first and third suction cup heads 1130 and 1134 (distal and label ends), which are equal in size.

The lifter head housing/plate can have a variety of shapes, including, for instance, substantially squared-shaped, substantially rectangular shaped, and cylindrically shaped (e.g., circular or oval). The housing or plate is also configured so the bottom surface of the plate (which has the suction cups and comes into contact with the coverslips) can have a variety of shapes, including, for instance, substantially squared-shaped, substantially rectangular shaped, and circular or oval shaped. This bottom surface can be flat, flat with one or more curves or bends, and the surface may have dimensions be relatively bigger, relatively smaller, or substantially identical to the dimensions of the specimen-bearing microscope slide. For instance, in one embodiment, the lifter head is a substantially rectangular shaped plate having a relatively flat bottom surface with dimensions similar or substantially identical to the dimensions of a standard rectangular shaped coverslip and having three small, individually plumbed suction cup heads arranged one after the other in a substantially straight line on the flat, bottom surface. Alternatively, the lifter head can be configured such that the bottom surface (i.e., the surface with the suction cups) is flat, curved, chamfered, beveled or any combination thereof.

Referring to FIG. 8, one lifter head configuration includes a flat bottom surface (square or rectangular-like) with 3 identical small suction cups. This designated the DE configuration One lifter head configuration can be a center concave design. Referring to FIG. 9, the concave design features a housing/main body with a flat bottom surface face with a center curve downward forming a "frown" configuration (like a frown icon). In one embodiment, suction cup heads can be the same size or different in size. In one embodiment, the lifter head features 2 small suction cup heads (distal/label) located outside the downward curve and 1 larger central suction cup head located in the center downward curve (between the two smaller outer suction cups).

Another lifter head configuration is a convex or "smile" mode/configuration design including the "dual chamfer narrow" lifter head and the "dual chamfer wide" lifter head. Referring to FIG. 11, a convex or "smile" mode features a housing/main body 1310 with a flat or partially flat bottom surface curving upward so the surface is convex or partially convex, forming a "smile" shape with the coverslip. In one embodiment, suction cup heads 1330, 1332, and 1334 can be the same size or different in size. This dual chamfer design employs 5 degree chamfer angles on the distal and proximal ends of each lifter head. Referring to FIG. 13, in the "dual chamfer narrow" design, the bottom surface plate has a reduced in size as compared to the remainder of the housing/plate main body of the lifter. In this regard, the convex curved bottom surface for the "dual chamfer narrow" is smaller in size relative to that of the "dual chamfer wide". This reduced width on the dual chamfer narrow design limits possible fluid contact with the lifter head. The fluid contact to avoid here is actually the result of excess solvent being "squeezed out" from between the coverslip and the specimen area of the slide, and then migrating to the top of the slide/coverslip combination. In one embodiment of the "smile design", the angle of both chamfers is 5 degrees and is set a distance in from the ends of the lifter head of 0.52 inches to the end of the chamfer. In one embodiment, for the "smile" mode, the middle cup is often at ambient pressure and the outer two cups would be pulling vacuum when holding the coverslip.

The concave and convex shapes imparted to the retained coverslips is mostly determined by the geometry induced by the vacuum on the suction cups. Both "frown" and "smile" modes are considered standard features and functions of the inventive coverslipper instrument and methods, respectively.

Referring to FIG. 3, the coverslipper contains one or more transport mechanisms. For instance, each lifter head is attached to one or more transport mechanisms (or transporters) coupled to one or more motors and is configured move each lifter head within the automated coverslipper. In this regard, the lifter head, coverslip cartridge, and slide tray (and any other component part) can be moved in orthogonal directions to accurately position the coverslips in the cartridge or slides relative to the path of travel of the lifter head. The transport mechanism can include, without limitation, one or more robotic arms, conveyors, plungers, motors (e.g., stopper motors, drive motors, etc.), rail assemblies (e.g., carriage and linear rail assemblies), controllers, combinations thereof, or the like, attached either directly or indirectly to the lifter heads. The components and configuration of the transport mechanism can be selected based on the desired movement of lifter head.

In one embodiment, referring to FIG. 3, transport mechanism is attached to, and suspended vertically from, a carriage platform attached to an overhead rail and reciprocally driven along the rail by a stepper motor-driven lead screw for example, attached to one or more lifter heads. In this embodiment, the lifter heads are also suspended vertically from the carriage platform in the coverslipper and can move between the coverslip cartridges and slides to perform various operations and functions, including applying adhesive solvent to the specimen, coverslip pickup, transport, placement and laydown of the coverslip on the target area of the specimen. This allows horizontal movement of the lifter head. In addition, a reciprocally vertically moveable plunger is also mounted on each lifter and extends along a vertical axis. The plunger is driven by a stepper motor-driven lead screw configured to raise and lower the lifter head in a substantially vertical direction to enable pick up of a coverslip from a cartridge and laydown of the coverslip on a slide. In one embodiment, referring to FIGS. 2 and 3, the coverslipper has two lifter heads positioned in tandem to work simultaneously on two rows of slides on the tray.

In some embodiments, two or more lifter heads can be attached to a lifter head assembly and transport mechanism (see FIG. 3 B). Each lifter head has independently plumbed lines that are fully addressable so, should operations require, the lifter head can pick up and roll down from either end of the coverslip. In this embodiment, the two lifter heads can have a same-way configuration, with the left and right lifter heads working simultaneously to address both rows of the slide tray in the same manner. In another embodiment, the lifter heads could be configured to operate as mirror images of one another.

In addition, each lifter head can be coupled or integrated with other devices, such as a fluid dispenser and an air knife. These devices, which are also attached to the transport mechanisms, perform various procedures, including slide preparation before coverslip laydown.

Fluid Dispensers—The lifter head assembly of the coverslipper further contains one or more fluid dispensers to dispense fluid in a manner to further minimize distortion due to bubble entraining, electrostatic charge and splashing. The fluid dispenser (see in FIGS. 6 and 7) can be integrated with or be configured to move with each lifter head and transporter—it may be part of the lifter head, be separate but attached to the lifter, or positioned next to the head and operate separately alongside the lifter head. In this regard, the fluid dispenser can move in tandem or separately with the lifter head. The fluid dispenser contains a moveable dispenser head with one or more nozzles (needles or outlets) in fluid communication (via fluid conduit lines with sensors and control valves) with a fluidic module for dispensing a precise and controlled amount of fluid at one or more points along the slide. Sensors and control valves control the type and amount of fluid dispensed. The fluid dispenser and slide tray can be moved in orthogonal directions to accurately position the slides relative to the path of travel of the fluid dispenser. The fluid dispenser head itself may also move vertically (which movement may be separate from the lifter head) to position the nozzles at a precise and controllable distance from a slide, if any, positioned in the coverslipper. The fluid dispenser can move or remain stationary as it dispenses fluid on the slide. For instance, the fluid dispenser may move along a path generally parallel to the longitudinal axis of the slide without ever touching the slide or the liquid on the slide. In one embodiment, the fluid dispenser dispenses fluid at eight central points on the slide. In another embodiment, it was found that a single dispense at the distal end of the slide, which relies on capillary gap action for subsequent dispersal, is sufficient to minimize bubbles and electrostatic charges that cause fluid irregularities like splashing and "jumping" of fluid on-slide and even off-slide.

The fluid dispensers can dispense a precisely controlled amount of fluid, such as a coverslipping mounting medium or an activator solvent for a pre-glued coverslip, onto the slide. For instance, the volume of coverslipping fluid dispensed during a single dispense is in a range of about 5 µl to about 80 µl, from about 10 µl to about 70 µl, from about 20 µl to about 60 µl, from about 30 µl to about 50 µl, and in one embodiment is about 20 µl. In one embodiment, the fluid dispenser contains one nozzle and makes 2 rapid dispenses of coverslipping liquid of about 20 µl to about 30 µl each (for a total of about 40 µl to about 60 µl) toward the distal end of the microscope slide (end without a label). In yet another embodiment, the total amount of coverslipping fluid dispensed is about 40 µl. In one embodiment, the coverslipper of the present disclosure employs a unique pre-glued coverslip that does well in the range of total solvent activator volume between 15 to 60 µl for a 1×2 inch coverslip. The optimal volume identified considering all of the specific requirements for the HE 600 is about 40 µl. This volume may be dispensed as a single dispense, or as multiple smaller volume dispenses at or near the same dispense location on the slide. One embodiment use 2 dispenses of 22 µl per coverslip. The advantage to this approach is the on slide fluid is more easily controlled and since the surface of the slide and sample ahead of the moving wave front of fluid is dry the discharge of static electricity induced in the coverslip by its deformation is significantly reduced. The inventors have discovered that static electrical discharges from the coverslip to a fluid surface can created bubble formation.

In one embodiment, a coverslipping liquid is used, which includes a terpene, such as a monoterpene (e.g., limonene). A coverslipping liquid selected or formulated in accordance with a particular embodiment of the present technology includes about 100% d-limonene with a suitable preservative, such as 500 parts per million butylated hydroxytoluene. Use of monoterpenes in the coverslipping liquid tends to be significantly less problematic than use of other reagents used in previous automated coverslippers. For instance, in at least some cases, the utilized amount of monoterpene coverslipping liquid is low enough that it fully evaporates after its use without causing noticeable noxious fumes. In these cases, since there may be no liquid monoterpene waste, there may also be no need for special protocols, if any, for remediating or handling of system waste liquids due to the presence of monoterpenes in these liquids. This "coverslipping liquid" is only a useful choice for a non-typical pre-glued coverslip. Essentially all other automated coverslippers employ coverslipping mounting media such as Poly-Mount brand acrylic polymer dissolved in xylene or toluene, though there are water- and limonene-based mediums commercially available.

In an automated coverslipper configured in accordance with embodiments of the present technology, the coverslipping liquid can be applied to specimens generally after the specimens have been stained, exit the stainer, and enter the coverslipper. A coverslipping liquid is first dispensed onto the slides and the dispensed coverslipping liquid is then removed. The coverslipping liquid can be dispensed on the slide or near the side edge of the slide and swept across the narrow dimension of the slide using an air knife. This can serve to remove any residual conditioning liquid remaining on the slides. Thereafter, the coverslipping liquid can be dispensed at or near one end of the slide as discussed previously.

Air Knife—In one embodiment, a multi-step dispense and assisted liquid movement (e.g., air knife assisted liquid movement) can be employed. In this regard, the coverslipper includes one or more liquid removal devices, including an air knife (or gas knife) or a suction element (this suction element is separate from the suction cups in the lifter head), which are coupled to, integrated with or merely associated with the lifter head so they will move with or synchronized to move in tandem. The gas knife and suction element are configured to cooperate to draw most or all of the volume of coverslipping liquid into the suction element. The gas knife can be a linear (e.g., uniplanar) gas knife or it can be V-shaped gas knife to partially surround the suction element. The gas knife can be used with a variety of suitable gases, such as air, nitrogen, air/nitrogen mixtures, or other gases compatible with processing liquids and tissue specimens. Though the term "air knife" may be used herein for ease of reference, unless the context clearly indicates otherwise, the term also refers to gas knives capable of producing gas curtains comprised of any suitable gases. The air knife can output streams of air (e.g., ambient air, filtered air, etc.) to produce an air curtain, streams of nitrogen to produce a nitrogen curtain, or streams of other gases to produce other types of gas curtains.

The gas knife is moveable and is attached to a transporter and can be integrated with the fluid dispenser and lifter head. The gas knife can include one or more sensors. The gas knife is configured to accurately position the gas knife into a position relative to the slide.

Referring now to FIG. 6, in one embodiment, the coverslipper utilizes an air knife (not shown) that employs a single extended slot approximately 2 inches wide by 0.002 inches high, directed at a 45 degree angle to the surface of the slide, situated approximately 0.10 to 0.15 inches above the slide.

After a coverslipping liquid has contacted the slide for a desired length of time, the gas knife can deliver one or more streams of gas toward one side edge of the slide to produce the gas curtain to force the liquid from the surface of the slide. The gas knife can be configured to produce the gas curtain using no more than one stream of gas or using two or more streams of gas. Before, during, or after moving the liquid removal device the suction element can contactlessly remove liquid from the slide. As the gas knife moves across the width of the slide, for example, the gas curtain can confine and move the volume of liquid away from a longitudinal edge of the slide to the other edge. Additional suction element could also be used to draw a partial vacuum to remove the liquid from the slide without physically contacting the slide.

The gas consumption/flow rate of the gas knife can be in a range of about 8 liters/minute to about 9 liters/minute, for example, about 8.6 liters/minute to provide an input gas knife pressure of about 7 psi+/−0.2 psi. Excessively high gas knife pressures or flow rates could lead to loss of removed liquid distribution (over wetting) or removal of the sample from the surface of the slide and excessively low pressures or flow rates could lead to residual high residual volumes. The gas knife and suction element cooperate to produce a pressure differential to urge the proximal region of the volume of liquid away from the side edges. In some embodiments, the gas knife and the suction element produce a low pressure region at least partially defining a collection zone in which the liquid tends to collect. The collection zone can be positioned directly below the inlet port of the suction element.

In another embodiment the liquid removal device can move along a processing path generally parallel to the longitudinal axis of the slide. The suction element can provide a partial vacuum to produce a low pressure region at the collection zone where the suction (flow) of the liquid can occur. A pressure gradient between the low pressure region and the ambient pressure, along with the gas flow interaction between the gas knife and the suction element, can urge the liquid toward the collection zone. A region of the upper surface positioned behind the gas curtain can be substantially free of the liquid. There may be, however, a small volume of residual liquid on the region, but most of the total volume of the liquid on the slide can be located between the gas curtain and the end of the slide. Depending on the characteristics (e.g., surface tension) of the liquid, most or substantially all of the volume of liquid can be kept in front of the gas curtain moving along processing path. As the gas curtain advances distally, the liquid tends to flow along the curtain portions, and the curtain portions, can urge outer portions, (FIG. 16B) of the puddle of liquid away from the longitudinal edge, respectively, to reduce the likelihood of liquid falling off the slide. Advantageously, the lengthwise movement and position of the gas curtain allows the lifter head assembly to be moved at relatively high speeds while keeping the volume of liquid on the slide.

The liquid removal process can be performed to remove most or substantially all the volume of liquid. In some embodiments, the liquid removal device can remove at least 90% of the volume of liquid on the upper surface. In other embodiments, the suction element and gas knife are configured to cooperate to remove at least 95%, 98%, or 99% by volume of liquid from the upper surface. Additionally or alternatively, the liquid removal process can be controlled based on target maximum residual volumes. In some embodiments, the liquid removal device can remove a sufficient volume of the liquid such that a maximum residual volume on the upper surface after liquid removal is less than the maximum residual volume. In one process, the volume of liquid on the upper surface can be about 0.5 mL to about 0.9 mL of processing liquid, and liquid removal device can remove a sufficient volume of liquid such that the maximum residual volume of liquid on upper surface is equal to or less than about 50 µL.

In some embodiments, the gas knife and suction element cooperate to draw the liquid from the slide while keeping a total volume of the liquid, if any, that falls off the slide equal to or less than a maximum fall-off volume. The fall-off volume can be equal to about 5%, 3%, or 2% by volume of a total volume of liquid on the slide prior the beginning the liquid removal process. As such, the gas knife and suction element can be configured to cooperate to draw at least about 95%, 97%, or 98% of the free-standing volume of the liquid (i.e., liquid located along the surface and not incorporated into the specimen) into the suction element.

Liquid waste can be delivered through lines and into waste containers. For example, the slide trays can collect any liquid waste, such as coverslipping liquids used to apply coverslips to the slides. The liquid waste is collected and pumped to waste containers which can be opened to access and empty the waste containers. Periodically removing this liquid waste can be useful to keep the waste from spilling out of the slide trays during handling.

Figure 17B:
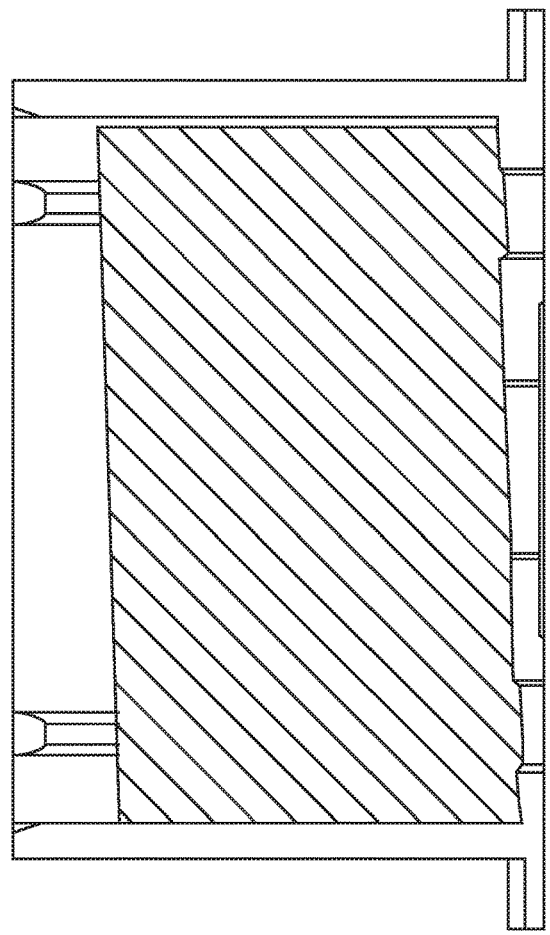
FIGS. 17 A-B depict a coverslip cassette loaded with a stack of coverslips, shown in an exploded view and in a cross-sectional view, illustrating the tilted aspect of the cassette interior floor.
Figure 17A:
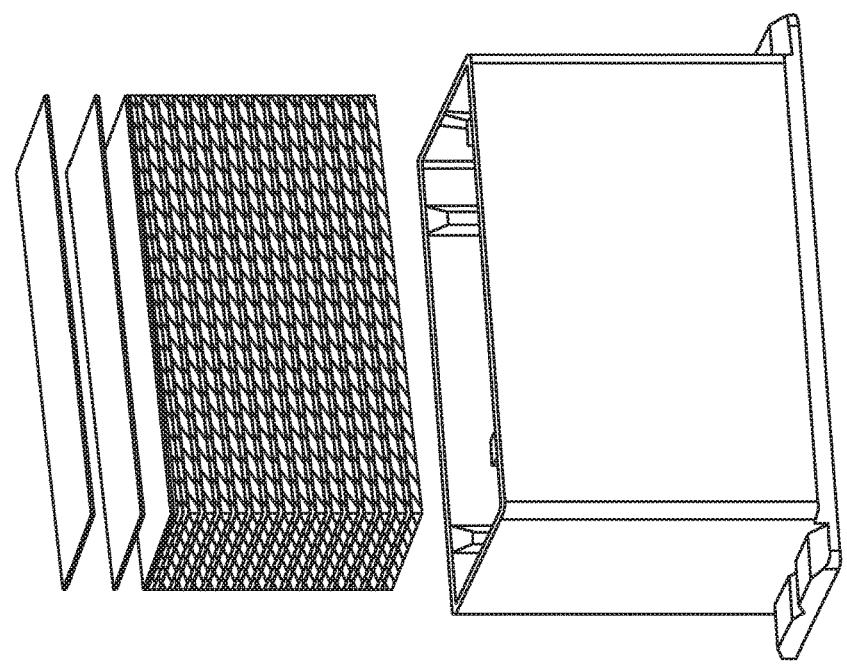

Coverslips—Referring to FIG. 17, in one embodiment, the coverslipper further includes a coverslip cartridge/cassette (FIG. 17 A), having an open dispensing end. The magazine defines a container configured to hold coverslips stacked in a substantially vertical arrangement. In one embodiment, the vertical stack of coverslips is titled at an angle (FIG. 17 B). For instance, the stack can be tilted downward into the lower right corner of the cassette (by design of the cassette) in which the stack is higher in the back of the cassette and higher to the left of the cassette. This 2.5 degree declination of the stack also helps to create a shear force from the approaching suction cup heads that have positive pressure.

The coverslips can be generally circular shaped, rectangular shaped, square shaped or any other suitable shape. In some embodiments, the coverslips are circular with diameters of 18 mm, 22 mm, or 25 mm. Square coverslips can have sides with lengths of about 18 mm, 22 mm, or 25 mm. Rectangular coverslips can have sides with lengths from about 11 mm×22 mm to about 48 mm×60 mm. The dimensions, shapes, and properties of the coverslips can be selected based on, for example, the size of the microscope slides. The coverslips can be made, in whole or in part, of transparent plastic, glass, or other transparent or semi-transparent materials. In a particular embodiment, the coverslips have a substantially planar top and bottom surface and a substantially rectangular configuration, with a length and a thickness slightly less than the specimen slide.

In a particular embodiment, the coverslips applied to slides are coated, on their bottom surface with an adhesive, such as a dry, activatable adhesive. The adhesive is activated by a solvent compatible with coverslipping that is placed on the slide by a fluid dispenser in the coverslipper. The activatable adhesives can be, for example, dry activatable toluene, xylene, or the like. Examples of dry, activatable adhesives include Permount™ (Fisher Scientific, Pittsburgh, Pa.) or ShurMount™ (Triangle Biomedical, Durham, N.C.). U.S. Pat. No. 6,759,011, describes a more particular example of a pre-glued coverslip that can be used in the coverslipper, and is incorporated by reference herein. In this regard, in one embodiment, the coverslipper uses pre-dried glued glass coverslips (i.e., glue that has been dried on to a controlled thickness). In an alternative embodiment, glue may be applied to slides (such as through dispense nozzles) prior to placement of a coverslip onto a slide.

Control Module—At least some embodiments include a control module allowing technician input. The control includes one or more computers (CPUs running software) and sensors in electrical communication with the component parts of the coverslipper, including, for instance, the lifter heads, fluid dispensers, air knives, sensors, transporters and motors, pneumatics module (e.g. vacuum source, control value, conduit lines and sensors), suction cups, the slide tray, etc. The control module receives and stores electronic data and software and coordinates all function and movement of the component parts of the apparatus.

Pre-Calibration—Often when installing the lifter head module and before inserting specimen-bearing slides into the device and running the coverslip application, a technician can (via the control module (and software)) initiates a calibration protocol to measure the various distances and dimensions between the lifter head, slide tray, and slide, and the coverslip in the cartridge, as well as the sizes and dimensions of the slides. For instance, using a blank slide without specimen, sensors on the coverslipper measure the height of the slides, as well as, maximum and minimum distances required for the lifter head to move in the device, for example, to move down to the slide. Tension of the rubber suction cups is also measured. Utilizing software on the control module, the coverslipper is then calibrated to include maximum and minimum safe movement distances of the various component parts. The pre-calibration step is important because the software driving the cantilever pick up and laydown processes relies heavily on known distances and tension of the rubber cups.

Coverslide Preparation—In at least one embodiment, when a slide tray containing one or more microscopic specimen slides is introduced into the coverslipper, a sensor integrated on the lifter head initiates a slide preparation protocol that, at first, includes an initial blow off using gas knife (integrated with the lifter head) to blow off any transfer fluids accumulated on the slide. This transfer fluid is simply fluid designed to keep the affixed histology sample hydrated between stations. After initial blow off, fluid dispenser dispenses a coverslipping liquid (such as limonene) utilizing a single or multi-point edge dispense. At this point, the treated slide is now ready for coverslip application. Alternatively, in some embodiments, a second blow off may be performed, whereby the applied coverslipping liquid is blown off and removed using the gas knife and suction element thereon to ensure any background fluid from this point forward, is actually the same fluid applied later as the actual solvent; and after the second blow-off, the coverslipping liquid is reapplied again several points down the center of the slide, or alternatively, the lifter head may employ a single dispense of fluid/solvent. The treated slide is now ready for coverslip application.

It is noted that the lifter head can be configured to perform coverslip preparation either before, during, or after coverslip pickup. In general, coverslip preparation is performed, where needed, before coverslip laydown.

In some embodiments, the automated coverslipper can be used in conjunction with, or it can be incorporated into as component part, a larger automated instrument for processing and analyzing biological specimens on microscope slides. Examples of such can be found in U.S. Pat. No. 7,271,006 (Reinhardt), U.S. Pat. No. 7,468,161 (Reinhardt), U.S. Pat. No. 7,727,774 (Reinhardt), and U.S. Pat. No. 8,048,373 (Reinhardt).

Cantilever Pick Up—As discussed previously, each pneumatics module is configured to supply a controlled, independent vacuum or pressurized gas to each suction cup sufficient to enable a cantilever pickup and a cantilever laydown of a coverslip on a slide or to apply one or more air bursts. Cantilever pickup basically involves 4 steps, illustrated in FIGS. 19 A-D how independently vacuums control the pickup process. In Step A, the lifter head 1818 bottom surface is lowered to a coverslip in the opening on the cartridge. At this point, upon touch down in coverslip cassette (or at a predetermined short distance hovering about the coverslip), only the label end of suction cup is activated with vacuum. In Step 2, the vacuum activated in the label end suction cup lifts and picks up one end of the top coverslip. This is known as cantilever mode because the coverslip is held only at one end, and this allows for a more efficient single coverslip lifting. In Step 3, after the label end of the coverslip is secured and lifted to the top of the coverslip cassette, vacuum is also activated in the center suction cup. In Step 4, vacuum is applied to the distal end suction cup head, so all three vacuums in all three suction cups are engaged. At this point, a pressure sensor determines the integrity of the lifted coverslip to find any breaks or leafs and to determine if more than one coverslip has been suctioned up. If there are no breaks and single coverslip has been lifted, the lifted coverslip is then ferried via the lifter head to the slide tray for application. At this point, the pressure sensor can be engaged once more to determine the integrity of the lifted coverslip just in case something happened to the coverslip while in transit.

For Cantilever Laydown—After once the minimum threshold is achieved, the lifted coverslip is transported to the slide tray and positioned above a specimen-bearing microscope slide to begin the process of laying the lifted coverslip onto the slide. The coverslip laydown process uses a reverse-peel or roll-down action that is, in fact, the result of the releasing the vacuum in the Distal End Suction Cup Head first. Last to engage during the pickup process, the Distal End Suction Cup Head releases its end first when positioned over the slide, using the control valve to slowly bleed off vacuum pressure. This results once again in a cantilevering effect. At this point, to prevent vibrational slapping that could disrupt proper flat (not parabolic) meniscal formation and, once again, entrain obfuscating bubbles, once the coverslip makes contact with the slide on the distal end, two things happen: 1) the vacuum on the center suction cup and the label suction cup head is very slowly bled off using the control valve; and 2) the bleeding off/release of the final two suction cup heads happens in one or more short and timed. This pulsing of coverslip laydown is critical to developing the flat meniscal dispersal needed to fully eradicate bubbling and ensure proper saturation with limonene. Accordingly, in this manner, as the vacuum in the remaining two suction cups is slowly bled off, the coverslip is gently laid down in a way that promotes optimal fluid dispersement with no bubbles. In one embodiment, the laydown process involves a highly controlled process of six incremental pulses where pressure is released and coverslip is rolled down 0.0018 inches every 200 milliseconds. This allows for optimal control and precision.

In a further embodiment, after the label-oriented end suction cup (corresponds to what would be the end of the slide that may have a label on it) that has bled off pressure and the last edge of the coverslip touches down, the lifter head applies one or more final bursts of pressured air from all three suction cup heads before the lifter head pulls upward. For instance, in one embodiment, a final, measured (100 ms) burst from all three suction cup heads is made before the lifter head begins pulling upward. This final burst of air helps to separate the coverslip from the lifter head, including any static attraction, without causing rotational torque (as might happen if just one cup were used), and it also helps squeeze any surplus solvent out the periphery of the coverslip-slide interface.

This process is optimal for controlled laydown. Dropping or slapping the coverslip down atop the slide using a three-cup release (as opposed to bleeding off vacuum) could not only entrain severe bubbling, but would also risk getting splash-back of solvent on the tray, the bottom of the slide and even on the suction cups themselves, which, in turn, would corrode the material over time and subsequently hamper future functioning, since the software driving this process relies heavily on known distances and tension of the rubber cups.

In one embodiment the coverslipper uses glass coverslips with a pre-applied dry mounting medium on them. A solvent (limonene) is applied to activate the dry mounting medium. The coverslips are applied from the distal end toward the label end of a slide using a wave of solvent to roll out any bubbles underneath the coverslip.

Various non-limiting embodiments will be discussed in the examples below. Such examples are non-limiting and merely representative of the technology disclosed herein.

EXAMPLE 1

In one embodiment, the coverslipper device performs a Pickup Stage, Laydown Stage, and Final Burst Stage. Referring to Figures, in the Pickup Stage, when the lifter head extracts a coverslip from the cassette, it does so only at one end—for this reason the process is called cantilever mode. For the purposes of the cassette cartridges, the "label end" suction cup head is opened to vacuum, while the remaining two suction cup heads are open to atmospheric pressure. In his regard, the "label end" refers to the suction cup head that will pick up the end of the coverslip that will ultimately be laid down on the label end side of the microscopic slide. The lifter head is lowered into the cassette, while the pressure is monitored on the label end suction cup until a pre-specified threshold pressure is achieved. This confirms the label side end of the coverslip has been firmly affixed to the label end suction cup. At this point, as the lifter head pulls up, the central suction cup head is also activated while the distal suction cup head remains open only to atmospheric pressure. As the lifter head lifts, the coverslip is peeled upwards and out of the cassette (lift-and-peel). Once this has been accomplished, the distal suction cup head's vacuum is engaged such that all three suction cup heads are now exerting the same amount of suction on the slide. This is when the total pressure is gauged through the associated sensor to determine if there are any breaks or tears in the slip. If the pressure does not achieve a minimum threshold, the coverslip is assumed defective or broken and is discarded, with the whole process repeated. If the minimum threshold is exceeded, two or more coverslips have likely been picked up and these will also be discarded. This is entire process involves a single coverslip extraction using cantilever mode.

Next, after the coverslip has been prepped (various fluids have been blown off, and the coverslipping liquid has been applied down the center, the lifter head will then attempt laydown the suctioned/lifted coverslip on a slide (the Laydown Stage. The coverslip laydown process uses a reverse-peel or roll-down action that is, in fact, the result of the releasing the distal suction cup head first. Last to engage during the Pickup Stage, the distal suction cup head releases its end first when positioned over the slide. At this point, to prevent vibrational slapping that could disrupt proper flat (not parabolic) meniscal formation (and, once again, entrain obfuscating bubbles), once the coverslip makes contact with the slide on the distal end, two things happen: (1) the vacuum on the center suction cup head and label suction cup head are very slowly bled-off using the control valve; and 2) the bleeding off/release of the final two suction cup heads happens in six short intervals that are purposely time-delayed by 200 milliseconds. This pulsing of coverslip laydown develops the flat meniscal dispersal needed to fully eradicate bubbling and ensure proper saturation with limonene fluid.

Next, in the Final Burst Stage, after the label suction cup head has been bled of pressure and the last edge of the coverslip touches down, the lifter head applies a final, measured (100 ms) burst from all three suction cup heads before the lifter head begins pulling upward. This helps separate the coverslip from the lifter head, including any static attraction, without causing rotational torque (as might happen if just one cup were used), and it also helps squeeze any surplus solvent out the periphery of the coverslip-slide interface.

EXAMPLE 2

In another embodiment, the coverslipper device also performs a Pickup Stage, Laydown Stage, and Final Burst Stage. Similar to that in the first example above, the lifter head of this second embodiment, utilizes three plumbed suction cup heads, each of which features dedicated pneumatic tubing with an independent control valve for maximum flexibility in handling. When a slide tray is introduced into the coverslipper module, the lifter heads initiate a protocol that, at first, includes using an air knife (integrated into the lifter head) to blow off transfer fluid accumulated on the slide. This transfer fluid is simply fluid designed to keep the affixed histology sample hydrated between stations. After initial blow off, the lifter head then disperses Limonene in a multi-point edge dispense. This, too, is blown across to slide to ensure any background fluid from this point forward, is actually the same fluid applied later as the actual solvent. After second blow-off, the lifter head then dispenses Limonene at several points down the center of the slide. The slide is now ready for the coverslip application.

In the Pickup Stage of this embodiment, each suction cup head can be turned to ambient or suction and settings may vary from cup to cup depending on the desired outcome. In some instances, lifting and separating slides from the cartridge is best achieved by activating suction in only the Distal Suction Cup Head ($3^{rd}$ of three cups) of the lifter head. This allows the head to suction the lowest end of the stack.

Once the end cup has secured the end of the coverslip, the remaining two suction cups are activated to produce a 'peeling' action, effectively scooping the coverslip up and away from the stack.

After lift-and-peel, a software protocol is run to check if the coverslip is broken. This is done with a vacuum sensor in the associated lifter head manifold that gauges whether the pressure is commensurate with a coverslip that is fully adhered to the bottom surface of the lifter head. If the pressure reading is too low, the lifter head automatically goes over to the waste belt and drops the coverslip. The process is then repeated until proper coverslip handoff can be confirmed.

In the Laydown Stage of this embodiment, the now-successfully lifted coverslip is then ferried with the lifter head along a conveyer track for deposit on top of a slide. At this point, as the lifter head lowers itself on top of the slide, the plumbed line is used as a bleed valve, slowly releasing one suction cup after the next such that the coverslip is effectively rolled down on top of the slide in a reverse-peel action. In this respect, the cups are used as actuators for positioning the coverslip properly. The coverslip is applied from the distal to label end. The rolling action of the slide ensures proper distribution of the solvent that has just been dispensed atop the slide.

In the Final Burst Stage of this embodiment, when the last corner of the coverslip has been released onto the slide, the lifter head applies a final burst of pressure from all three cups to help squeeze excess Limonene out the periphery of the coverslip/slide interface. This pressure burst helps eliminate bubbles by forcing them out edges. It also breaks contact between the lifter head and the now-conjoined coverslip/slide.

EXAMPLE 3

This example illustrates another embodiment of the disclosure. In this example, each lifter head has three individually plumbed suction cups with pneumatic tubes leading to a manifold, where there is also a sensor that gauges pressure related to the three cups. Each cup also has a control valve or bleeder valve that allows for gradual changes in pressure or suction. Each suction cup can be turned to ambient suction or pressure, and actual settings may vary from cup to cup depending on the desired outcome.

In the Pickup Stage of this embodiment, the lifting and separating slides from the cartridge is best achieved by first activating suction in only the Label Suction Cup Head (first of three) of the lifter head. This allows the Label Suction Cup Head to suction the lowest (label) end of the stack. Once the Label Suction Cup Head has secured the end of the coverslip, as the lifter head retracts from the slide, the second suction cup is he activated to produce a 'peeling' action, effectively scooping the coverslip up and away from the stack, at which point the distal cup engages suction to fully affix the coverslip against the bottom surface of the lifter head.

In this embodiment, the Pickup Stage basically involves 4 steps that illustrate how vacuums control the pickup process. In Step 1, upon touch down in coverslip cassette, only the label end of suction cup is activated with vacuum. In Step 2, the vacuum from label end suction cup lifts just one corner of the top coverslip. This is known as cantilever mode because the coverslip is held only at one end, and this allows for a more efficient single coverslip lifting. Testing revealed that having vacuum in all three suction cup heads frequently lifted more than one coverslip at a time. In Step 3, after the label end of the coverslip is secured and lifted to the top of the coverslip cassette, vacuum is also activated in the center suction cup. In Step 4, all three vacuums in all three suction cup cups are engaged. This is where pressure is gauged to determine if the lifted coverslip is broken. The lifted coverslip is then ferried via the lifter head to the slide tray for application.

In the Laydown Stage of this embodiment, the laydown process uses the reverse pressure sequence to lay the coverslip atop the slide. It releases the Distal Suction Cup Head first using the control valve to very slowly bleed off vacuum pressure. It then slowly bleeds off the remaining two suction cup heads so that the coverslip is gently laid down in a way that promotes optimal fluid dispersement with no bubbles. It is, in fact, a highly controlled process of six incremental pulses where pressure is released and the slide is rolled down 0.0018 inches (0.04572 mm) every 200 milliseconds. This allows for optimal control and precision.

In the Final Burst Stage of this embodiment, after the label cup has been bled of pressure and the last edge of the coverslip touches down, the lifter head applies a final, measured (100 ms) burst from all three cups before the lifter head begins pulling upward. This helps separate the slip from the lifter head, including any static attraction, without causing rotational torque (as might happen if just one cup were used), and it also helps squeeze any surplus solvent out the periphery of the coverslip-slide interface.

EXAMPLE 4

This example illustrates another embodiment of the disclosure. As previously discussed, the lifter head can be configured such that the bottom surface (i.e., the surface with the suction cups) is flat, curved, chamfered, beveled or any combination thereof. The configuration of the bottom surface of the lifter was found to impact the coverslipping process. For instance, lifter heads having a flat surface bottom were found to be more susceptible to static between coverslips in the cassette and often lifted up more than one coverslip even with cantilevered one-cup suction. Another problem was how to lift and separate single slides in a reliable, reproducible way and how to lay them down gently (no dropping or slapping) since that causes fluid splash and usually entrains babbles. Accordingly, several differently designed lifter heads were tested.

One lifter head configuration that showed promise was a lifter head with a concave design. Referring to FIG. 10, the concave design features a housing/main body with a flat bottom surface face with a center curve downward forming a center concave configuration (like a frown icon). In addition, the head features 2 small suction cup heads located outside the downward concave curve and 1 larger central suction cup head located in the center downward concave curve (between the two smaller outer suction cups). All suction cups are individually plumbed and arranged one after the other along the bottom surface of the lifter head. Testing revealed that that coverslip separation under this design was more robust to static. Additionally, the force exerted on the coverslip under this design was enhanced due to the bigger center cup. This meant once cantilevered and extracted out of the cassette, the central (and most powerful) cup exerted such a strong vacuum on the coverslip, that the coverslip also demonstrated the same downward concave curve of the lifter head, mimicking the frown-shape. In other words, the concave configuration causes the coverslip to bend in a downward fashion which discourages static attraction with other slides. This actually proved helpful in decoupling any clung secondary coverslips at this point. In this manner, the center frown configuration causes the coverslip to bend in a downward fashion which discourages static attraction with other slides. The concave design was shown to be very effective at ensuring perfectly separated single pickups of coverslips.

An alternate possible configuration for the lifter head that can be implemented in the coverslipper according to user need is a convex or "smile" mode. This embodiment includes the "dual chamfer narrow" design (FIG. 12) and the "dual chamber wide" (FIG. 13). Referring to FIGS. 11 and 12, a convex or "smile" mode features a housing/main body with a flat or partially flat bottom surface curving slightly upward so the surface is convex or partially convex, forming a "smile". In one embodiment, suction cup heads can be the same size or different in size.

Of the types tested, it was found the "dual chamfer narrow" to be the optimal solution to the question of controlled coverslip laydown. Key to this controlled application is that the simple 5 degree chamfer angles on the distal and proximal ends of each lifter head actually provided more control over the dangle of the coverslip during cantilevering.

This helped eliminate the "s" curve on laydown for low-stress, controlled placement atop the slide. With the "dual chamfer narrow" lifter head, it was found that varying pressures produced significantly different and often improved results with coverslip lifting and application. In addition, the reduced width on the "dual chamfer narrow" lifter head limits fluid contact with the lifter head.

During testing, in the final step when the coverslip is released (in either smile or frown mode) all three cups exert a very slight pressure to help push off the lifter head and squeeze the last bit of solvent out the perimeter of the now conjoined coverslip/slide. As the coverslip is released a burst of air is applied with all three cups simultaneously; the use of all cups prevents rotational torque as the lifter head pushes off and helps squeeze out additional solvent (for more details on coverslip pickup and laydown, see separate write-ups).

Both "smile" and "frown" modes are considered standard features of the coverslipper instrument. It was determined that, when compared to each other, a convex or "smile" mode exhibits slightly superior results with controlled coverslip laydown; and the concave or "frown" mode exhibits slightly superior single slip pickup reliability.

EXAMPLE 5

This example illustrates yet another embodiment of the coverslip pick up and retrieval steps. Step 1: Touch down to Detect—Referring to FIG. 19 A-D, in this step, the label oriented suction cup (right arrow) is first opened to vacuum, while the Distal Suction Cup Head (left arrow) and the Center Suction Cup Head (middle arrow) are open to atmospheric pressure. The lifter head is then lowered (in direction of black arrow) into cassette, while the coverslipper is monitoring the Label Suction Cup Head pressure (right arrow) for a pre-specified target threshold pressure to be achieved. Achieving this threshold confirms the coverslip has been firmly affixed to the Label Suction Cup Head due to the vacuum. Once the threshold value is achieved, the lifter head descends an additional amount up to 0.050 inch to compress the Distal and Center cups. For this embodiment, the stack of coverslips is tilted downward into the lower right corner of the cassette (by design of the cassette) in which the stack is higher in the back of the cassette and higher to the left of the cassette. This 2.5 degree declination of the stack also helps to create a shear force from the approaching suction cups that have positive pressure. Step 2: Lift to Peel—At this point, the lifter head direction is reversed and a small movement of 0.150 inches (upward) from the stack is implemented. This causes a peel force from stack while the Distal Suction Cup Head (left arrow) and the Center Such Cup Head (Center Arrow) provide a force maintaining coverslip contact with the stack at the Distal end. Step 3: Pull Up to Center & Distal Cups—At this point, the Center Suction Cup Head and Distal Suction Cup Head are opened to vacuum pressure sequentially (with the Central Suction Cup Head going before the Distal Suction Cup Head). This causes the coverslip to pull up at the center position and finally, the distal position, resulting in a relatively flat coverslip pulled completely against the head. Step 4: Cantilever from Distal Cup—The Label Suction Cup Head and Center Suction Cup Head are turned off to vacuum. This creates a cantilever orientation of the coverslip adjoined only on the Distal Suction Cup Head end and the lowered end of the coverslip resting on the lowest portion of the stack. Step 5: Detect Good Coverslip—The Center Suction Cup Head and Label Suction Cup Head are turned on to vacuum again sequentially, which pulls the coverslip completely up against the vacuum head. At this time, all suction cup heads are checked for a target vacuum threshold to be achieved. All three suction cup heads now are exerting the same amount of suction on coverslip to fully affix it against the bottom surface of lifter head. At this time, all suction cup heads are checked for a target vacuum threshold to be achieved. If the minimum threshold is achieved, the lifted coverslip is transported to the slide tray for application to specimen-bearing microscopic slide.

As previously stated, detailed embodiments of the present invention are disclosed herein; however, it is to be understood that the disclosed embodiments are merely exemplary of the invention that may be embodied in various forms. It will be appreciated that many modifications and other variations stand within the intended scope of this invention as claimed below.

The invention claimed is:
1. An automated coverslip system for mounting a coverslip on a slide, comprising:
at least one coverslip;
at least one slide containing a biological specimen; and
at least one lifter head comprising a plate having a bottom surface with at least three individually controlled suction cups arranged thereon, each of said suction cups being fluidly connected, by way of a gas conduit, to a pneumatics module, which includes a vacuum source, a pressure source, a pressure sensor, and an independently operable control-valve for each gas conduit, said pneumatics module being configured to supply an independent vacuum or pressurized gas to each suction cup to enable the lifter head to pick up, transport, and deposit the coverslip on the slide, and wherein at least one of said independently operable control-valves is configured to allow both an immediate release of vacuum and a gradual release of vacuum.
2. The coverslip system of claim 1, further comprising:
a transporter coupled to a motor and attached to, and suspending, the lifter head in a substantially vertical position, and configured to move the lifter head horizontally, vertically, or diagonally to position the bottom surface of the lifter head over a coverslip; and
a control module in electrical communication with the transporter, the lifter head, the pneumatics module, and the suction cups, wherein the control module coordinates all functions of or interactions with each of the components of the coverslip system.
3. The coverslip system of claim 2, wherein the transporter and the control module are further configured to position the bottom surface of the lifter head over the slide.
4. The coverslip system of claim 2, further comprising:
at least one fluid dispenser associated with the lifter head and in fluid communication with a fluidics module that supplies a reagent to the fluid dispenser, said fluid dispenser configured to dispense fluid on the slide; and
at least one gas knife associated with the lifter head and in fluid communication with a pneumatics module and configured to provide gas to the top surface of a slide;
wherein the fluid dispenser and the gas knife are suspended in a substantially vertical position and the fluid dispenser and gas knife are configured to move with the lifter head, and wherein the fluid dispenser and said gas knife are in electrical communication with the control module.
5. The coverslip system of claim 4, wherein the at least one fluid dispenser and the at least one gas knife are associated with each other and the lifter head.
6. The coverslip system of claim 5, wherein the association of the at least one fluid dispenser, the at least one gas knife, and the lifter head is a physical coupling.
7. The coverslip system of claim 1, further comprising:
at least one slide tray holding, in a substantially horizontal orientation, at least two slides arranged in at least one row; and
at least one cartridge containing a plurality of coverslips vertically stacked and arranged so the top-most coverslip of the stack is accessible to the lifter head via a top opening in the cartridge.
8. The coverslip system of claim 7, wherein the at least one tray comprises at least two rows of slides.
9. The coverslip system of claim 8, wherein the at least one cartridge and stack of coverslips is configured to tilt the stack of coverslips at one or more angles.
10. The coverslip system of claim 8, wherein said coverslip system comprises at least two lifter heads positioned to work simultaneously or independently on at least two rows of slides.
11. The coverslip system of claim 1, wherein the bottom surface of the lifter head is flat, or flat with one or more curves or bends.
12. The coverslip system of claim 1, wherein the bottom surface of the lifter head has a shape selected from the group consisting of flat, concave, convex, dual chamfer and combinations thereof.
13. The coverslip system of claim 12, wherein said lifter head is configured to provide, either simultaneously or sequentially, an independent vacuum to each of the three suction cups to thereby hold the coverslip in various configurations to the bottom surface of the lifter head.
14. The coverslip system of claim 1, wherein said lifter head further comprises two or more vacuum sensors to measure vacuum pressure on said suction cups one or more times.
15. The coverslip system of claim 1, wherein said lifter head is configured to remove the vacuum in two of the three suction cups one at a time so one end of the coverslip is released and first laid onto the slide and the remainder of the coverslip is then rolled down onto said slide and thereby inducing a curvature in the coverslip.
16. The coverslip system of claim 15, wherein said lifter head is further configured to reduce the vacuum to the coverslip holding suction cup until the curvature in the rolled down coverslip is reduced and thereafter removing the vacuum to fully release the coverslip.

17. The coverslip system of claim 7, wherein the top opening of the cartridge is sized to allow the lifter head access to the coverslips therein.

18. The coverslip system of claim 1, wherein the pressure sensor is sufficiently sensitive to determine the presence of a coverslip or the presence of a broken coverslip.

19. A method for performing a laydown of a coverslip on a specimen-bearing microscope slide, said method comprising:

positioning a suction lifted coverslip over the slide, wherein the suction lifted coverslip is held to a bottom surface of a lifter head by a vacuum in three individually controlled suction cups arranged on said bottom surface, wherein each suction cup is fluidly connected, by way of a gas conduit, to a pneumatics module, which includes a vacuum source, one or more vacuum sensors, and a control-valve for each gas conduit, wherein said pneumatics module is supplying an independent vacuum to each of said three suction cups thereby holding said coverslip to the bottom surface;

dispensing fluid near one end of the slide;

removing the vacuum in two of the suction cups so the coverslip is held at one end only by the one suction cup that still has a vacuum;

lowering the coverslip to the surface of the slide and fluid dispensed thereon until a bend or curvature is induced in the coverslip thereby creating fluid movements across the surface of the slide whereby the coverslip is continually lowered and a wavefront of fluid created on the slide as the fluid is gently pushed from one end of slide to the other end; and releasing the final end of the slide by activating the vacuum valve to the suction cup holding the coverslip such that the vacuum is removed at a gradual release rate as opposed to an abrupt release.

20. The method of claim 19, further comprising one or more mechanically pulsed movements to slowly lower the coverslip onto the slide.

21. The method of claim 19, further comprising applying one or more bursts of deionized air through said suction cups to further discourage static electricity events and to squeeze out remaining excess fluid.

* * * * *